(12) United States Patent
Hersam et al.

(10) Patent No.: US 10,994,016 B2
(45) Date of Patent: May 4, 2021

(54) GRAPHENE OXIDE MEDIATED CELLULAR DELIVERY OF GADOLINIUM-LABELED MOLECULES

(71) Applicant: Northwestern University, Evanston, IL (US)

(72) Inventors: Mark C. Hersam, Wilmette, IL (US); Thomas J. Meade, Wilmette, IL (US); Hsiang-Hua Hung, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 15/251,681

(22) Filed: Aug. 30, 2016

(65) Prior Publication Data

US 2017/0074859 A1 Mar. 16, 2017

Related U.S. Application Data

(60) Provisional application No. 62/218,991, filed on Sep. 15, 2015.

(51) Int. Cl.
| | |
|---|---|
| *A61K 47/30* | (2006.01) |
| *A61K 49/08* | (2006.01) |
| *A61K 49/12* | (2006.01) |
| *A61K 47/54* | (2017.01) |
| *A61K 47/69* | (2017.01) |
| *A61K 49/10* | (2006.01) |
| *B82Y 5/00* | (2011.01) |

(52) U.S. Cl.
CPC ........ *A61K 47/547* (2017.08); *A61K 47/6921* (2017.08); *A61K 47/6923* (2017.08); *A61K 49/08* (2013.01); *A61K 49/105* (2013.01); *A61K 49/108* (2013.01); *B82Y 5/00* (2013.01); *Y10S 977/906* (2013.01)

(58) Field of Classification Search
None
See application file for complete search history.

(56) References Cited

U.S. PATENT DOCUMENTS

| | | | |
|---|---|---|---|
| 2013/0079503 A1* | 3/2013 | Lee | C07F 5/00 534/16 |
| 2015/0283239 A1* | 10/2015 | Lee | A61K 9/143 424/489 |

FOREIGN PATENT DOCUMENTS

| | | | | |
|---|---|---|---|---|
| WO | 2006112723 A1 | 10/2006 | | |
| WO | WO 2015/121150 | * | 2/2014 | C01B 31/04 |

OTHER PUBLICATIONS

Yang, X., et al. J. Phys. Chem. C (2008), 112; pp. 17554-17558.*

(Continued)

*Primary Examiner* — Kevin S Orwig
(74) *Attorney, Agent, or Firm* — Locke Lord LLP; Tim Tingkang Xia, Esq.

(57) ABSTRACT

A method of bioactive molecule delivery includes providing a first aqueous medium comprising native graphene oxide and a second aqueous medium comprising a bioactive molecular component that includes Gd(III)-labeled molecules; mixing said first and second media to form a mixture thereof; co-incubating the mixture for a first period of time for coupling said molecular component on a surface of said native graphene oxide, to provide a co-incubation product; and contacting a cellular medium with said co-incubation product for a second period of time for cellular delivery of said bioactive molecular component.

8 Claims, 17 Drawing Sheets

(56) References Cited

OTHER PUBLICATIONS

Deyhimihaghighi, N., et al. J. Phys. Conference Series (2014), 546; pp. 1-5.*
Venkatesha, N., et al. Mat. Res. Express 1 (2014) 045008; pp. 1-9.*
Shen, A.-J., et al. J. Biomed. Mater. Res. A (2012), 100(9); pp. 2499-2506; Epub May 24, 2012.*
Ren, X., et al. RSC Adv. (2014), 4; pp. 53987-53992.*
Liu, J., et al. Acta Biomaterialia (2013), 9; 9243-9257.*
Hong, V et al., "Analysis and Optimization of Copper Catalyzed Azide—Alkyne Cycloaddition for Bioconjugation", Angew. Chem. Int. Ed. 2009, 48, 9879-9883.
Chan, T. R. et al., "Polytriazoles as Copper(I)-Stabilizing Ligands in Catalysis", Org. Lett. 2004, 6, 2853-2855.
Mastarone, D. J. et al., "A Modular System for the Synthesis of Multiplexed Magnetic Resonance Probes" J. Am. Chem. Soc. 2011, 133, 5329-5337.
Manus, L. M. et al., "Gd (III)-Nanodiamond Conjugates for MRI Contrast Enhancement", Nano Lett. 2009, 10, 484-489.
Hung, A. H. et al., "Mechanisms of Gadographene-Mediated Proton Spin Relaxation", J. Phys. Chem. C 2013, 117, 16273 16263.
Lerf, A. et al., "Structure of Graphite Oxide Revisited", The Journal of Physical Chemistry B 1998, 102, 4477-4482.
Gao, W. et al., "New Insights into the Structure and Reduction of Graphite Oxide", Nat. Chem. 2009, 1, 403-408.
Sun, X. et al., "Nano-Graphene Oxide for Cellular Imaging and Drug Delivery", Nano. Res., 2008, 1, 203, 212.
Shen, H. et al., "PEGylated Graphene Oxide-Mediated Protein Delivery for Cell Function Regulation", ACS Appl. Mater. Interfaces 2012, 4, 6317-6323.
Liu, Z. et al., "PEGylated Nanographene Oxide for Delivery of Water-insoluble Cancer Drugs", J. Am. Chem. Soc., 2008, 130, 10876-10877.

* cited by examiner

Figure 9A
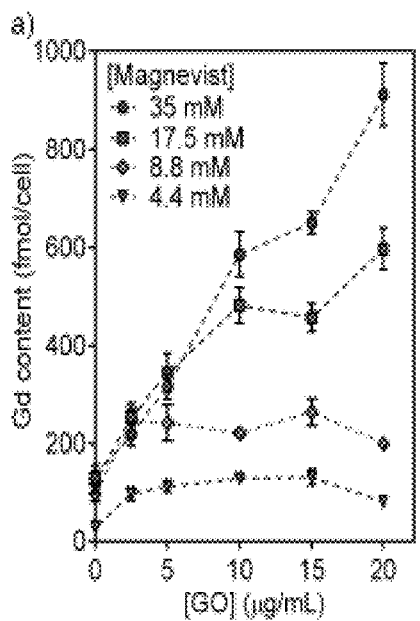
Figure 9B
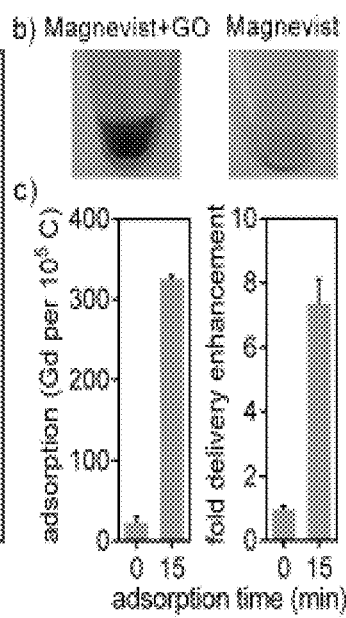
Figure 9C

Figure 10A
Figure 10B
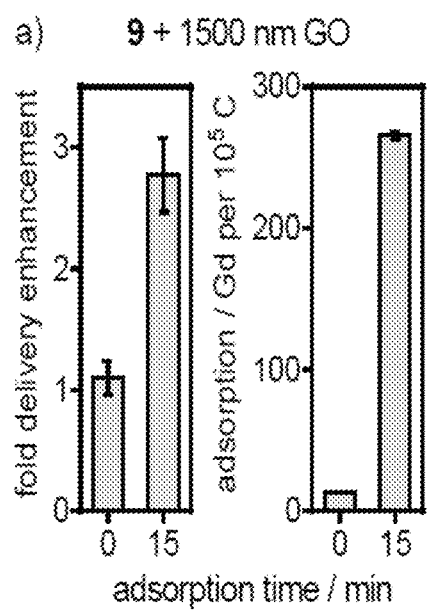
a) 9 + 1500 nm GO
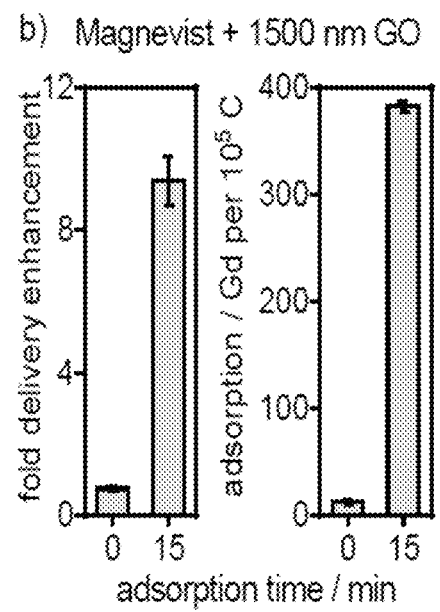
b) Magnevist + 1500 nm GO

GRAPHENE OXIDE MEDIATED CELLULAR DELIVERY OF GADOLINIUM-LABELED MOLECULES

This application claims priority to and the benefit of application Ser. No. 62/218,991 filed Sep. 15, 2015—the entirety of which is incorporated herein by reference.

This invention was made with government support under R01 EB005866, R01 EB014806 and U54 CA151880 awarded by the National Institutes of Health; and DBI1266377 awarded by the National Science Foundation. The government has certain rights in the invention.

BACKGROUND OF THE INVENTION

Graphene oxide (GO) is a two-dimensional mosaic of hydroxyls, epoxides, carbonyls, and aromatic rings. Its specific surface area surpasses that of other nanomaterials by 10-fold and encroaches on the theoretical maximum. These quintessential surfaces non-covalently interact with each other and with molecules in solution through a rich, multivalent combination of hydrogen bonding, charge interactions, $\pi$ chemistry, and hydrophobic effects. The unparalleled surface area and the diverse surface chemistry make GO an attractive platform as a cellular delivery vehicle.

Recently, surface-modified GO has been shown to deliver a variety of molecules, with hydrophobic drugs and single-stranded DNA being the most actively explored. However, an incomplete understanding of the GO system and the synthetic proficiency required to produce the nanocomplexes have hindered the adoption of these approaches by the larger biomedical community. Of equal importance, hydrophilic small molecules as a class have been largely overlooked in the studies of GO delivery thus far due to the presumed critical role of $\pi$-$\pi$ stacking and hydrophobic effects in the cargo-GO interaction.

SUMMARY OF THE INVENTION

In light of the foregoing, it can be an object of the present invention to provide graphene oxide delivery of hydrophilic small molecules and therapeutic agents, thereby promoting better understanding of such a graphene oxide delivery system, to overcome various deficiencies and shortcomings of the prior art.

Various objects, features, benefits and advantages of the present invention will be apparent from this summary and descriptions of various preferred embodiments, and will be readily apparent to those skilled in the art having knowledge of drug delivery systems. Such objects, features, benefits and advantages will be apparent from the above as taken into conjunction with the accompanying examples, data, figures and all reasonable inferences to be drawn therefrom.

In part, the present invention can be directed to a method for delivery of a hydrophilic small molecule. Such a method can comprise providing an aqueous medium comprising unmodified graphene oxide and an aqueous medium comprising a hydrophilic bioactive molecular component; mixing such media; co-incubating such a mixed medium for a time sufficient for coupling, binding and/or adsorbing such a molecular component on an unmodified graphene oxide surface, to provide a co-incubation product; and contacting a cellular medium with such a co-incubation product for a time sufficient for cellular delivery of such a hydrophilic bioactive molecular component. In certain non-limiting embodiments, such a molecular component can comprise a moiety selected from alkyl, amine, hydroxy, phosphate, carboxy, quaternary amine and aminoalkyl moieties and combinations thereof. Regardless, such a molecular component can be conjugated with an MM contrast agent to monitor and/or quantify delivery.

In certain embodiments, such unmodified graphene oxide can have a lateral surface dimension of up to about 1,500 nm or more. In certain such embodiments, such a lateral dimension can be about 150 nm or less, such a dimension as can provide more O-containing moieties and/or larger surface to edge ratio as compared to graphene oxide with a larger lateral dimension. Such an unmodified graphene oxide medium can, optionally, have a concentration up to about 20 µg/ml, such a concentration as can be utilized to optimize delivery. Regardless, in certain other embodiments, such contact can induce sedimentation of such a co-incubation product, to affect, modulate and/or enhance delivery of such a hydrophilic bioactive molecular component. In certain such embodiments, such a graphene oxide lateral surface dimension can be greater than about 150 nm.

In part, the present invention can also be directed to a method of using co-incubation to affect, modulate and/or enhance delivery of a hydrophilic small molecule. Such a method can comprise mixing an aqueous medium comprising unmodified graphene oxide and an aqueous medium comprising a hydrophilic bioactive molecular component; co-incubating such a mixed medium for a time sufficient for coupling, binding and/or adsorbing such a molecular component on an unmodified graphene oxide surface, to provide a co-incubation product; and contacting a cellular medium with such a co-incubation product for a time sufficient for cellular delivery of such a hydrophilic bioactive molecular component. Such a molecular component can comprise a moiety such as that described above or illustrated elsewhere herein. In certain such embodiments, such a molecular component can be conjugated with an MRI contrast agent to monitor and/or quantify cellular delivery thereof.

In certain embodiments, unmodified graphene oxide can have a lateral surface dimension of the sort discussed above or illustrated elsewhere herein. In certain such embodiments such a lateral dimension can be less than about 150 nm to about 1,500 nm or more. Regardless, such contact can induce sedimentation of such a co-incubation product, to affect, modulate or otherwise enhance delivery of such a hydrophobic bioactive molecular component.

In part, the present invention can also be directed to a composition comprising an unmodified graphene oxide nanoparticulate and a hydrophilic bioactive molecular component coupled thereto, such a nanoparticulate absent and unmodified by a polymer component and comprising a surface component having a lateral dimension up to about 1,500 nm or more. In certain non-limiting embodiments, such a graphene oxide surface component can have a lateral dimension of about 150 nm or less. In certain such embodiments, such a composition can be provided in an aqueous medium at a concentration up to about 20 µg/ml.

BRIEF DESCRIPTION OF THE DRAWINGS

FIGS. 9A-C. Delivery by GO is A) dose-dependent, B) observable by cell coloration, and C) abolished without sufficient adsorption time. Co-incubation enabled the independent control of molecular and GO concentrations. The use of Magnevist in the mM range is 100-fold greater compared to purified Magnevist-GO complexes. The 150 nm GO was used for the studies. Error bars show SEM.

FIGS. 10A-B. Additional adsorption time studies. FIG. 9C showed that both molecular adsorption and delivery enhancement were abolished when a Magnevist-150 nm GO mixture was added directly to media without allowing for adsorption time. The same result was found with a mixture of A) 9+1500 nm GO and B) Magnevist+1500 nm GO. Experiments were performed with 188 µM Gd(III) concentration and 18.8 µg/mL GO incubation concentration. Error bars show SEM.

DETAILED DESCRIPTION OF CERTAIN EMBODIMENTS

Figure 1:
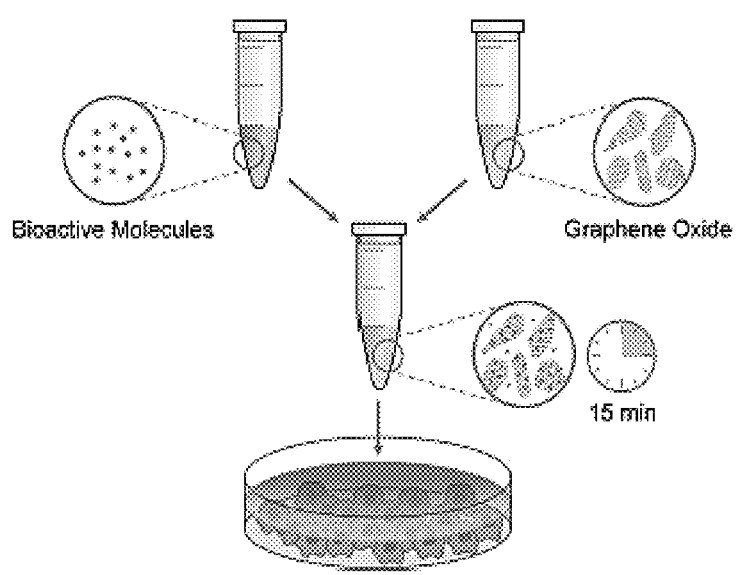
FIG. 1. The cellular delivery of bioactive molecules can be enhanced by simple mixing and co-incubation with graphene oxide in culture.

As relates to and illustrating certain embodiments of this invention and to expand the practical horizons of GO cellular delivery, native GO was used to deliver 14 illustrative hydrophilic, Gd(III)-labeled small molecules by co-incubation in culture (FIG. 1). Fundamentally, the Gd(III) labels and the chemical variety enabled a quantitative understanding of the molecular adsorption and delivery process. Practically, the use of unmodified GO allowed for the unconventional exploitation of sedimentation in delivery, while the co-incubation approach enabled the use of extremely high molecular incubation concentrations. To demonstrate the advantages of these properties, GO co-incubation was evaluated in the application of Gd(III) cellular MM. The systematic studies performed allow the generalization of GO co-incubation to other molecular cargos and applications. The simplicity of the described strategy makes it immediately accessible to the biomedical community at large.

Figure 2:
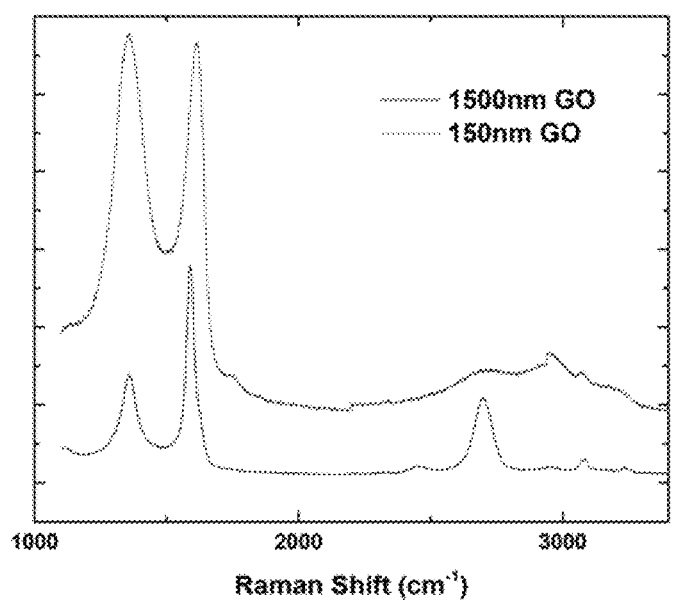
FIG. 2. Raman spectroscopy of the two graphene oxide preparations used for cellular delivery studies. Spectra are vertically staggered for clarity. The approximate Raman shift of the D, G, 2D and D+G bands are 1350 cm-1, 1584 cm-1, 2700 cm-1, and 2934 cm-1, respectively.
Figure 3:
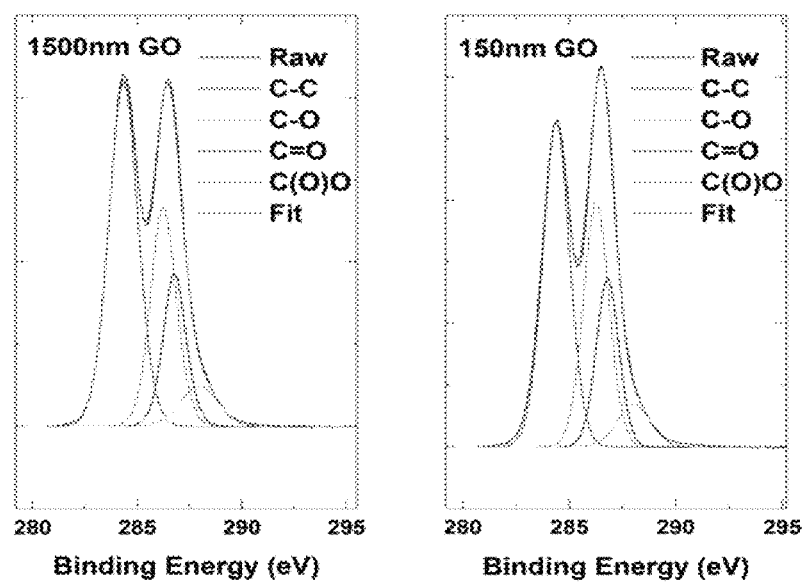
FIG. 3. X-ray photoelectron spectroscopy of the two graphene oxide preparations used for cellular delivery studies. The 150 nm GO contains 10%-15% more oxygen groups compared to the 1500 nm GO.
Figure 4:
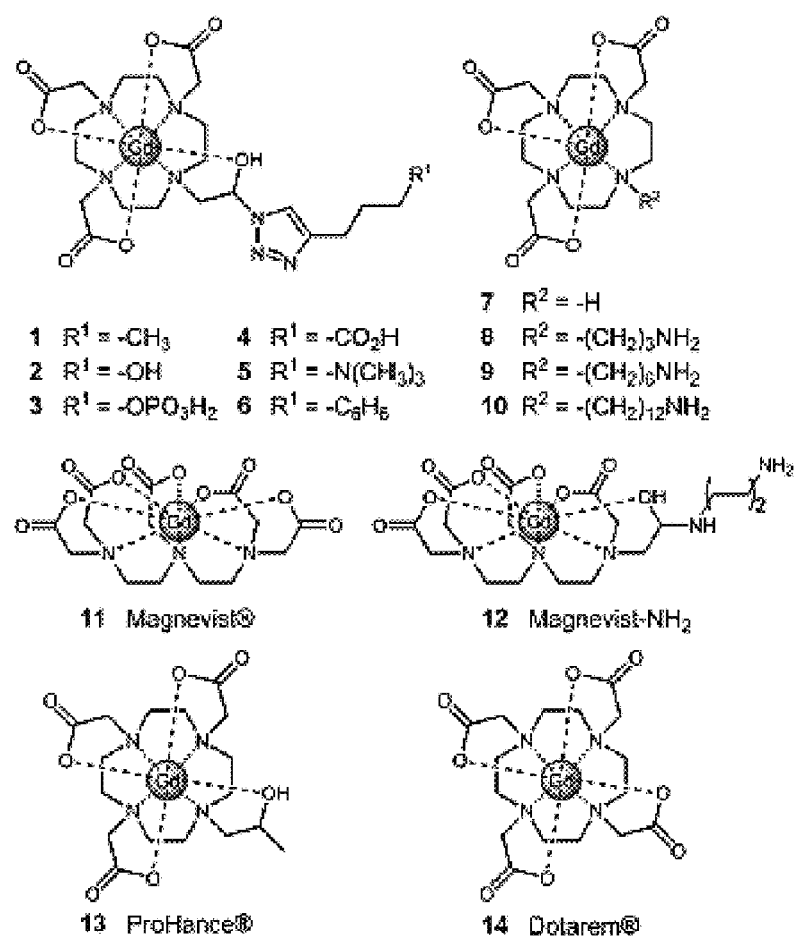
FIG. 4. Structures of the 14 molecules tested with GO for adsorption, sedimentation, and cellular delivery. The quenching properties of GO usually hinder quantitative studies. The challenge is overcome by using Gd(III) to enable analytical quantitation by ICP.

Two GO sizes with characteristic lateral lengths of 150 nm or 1500 nm were studied. Both samples were unmodified single sheets (Table 1) with similar chemical compositions consisting of an average C—C:C—O:C=O:C(O)O distribution of 10:5.5:4.1:1.4 (FIGS. 2-3). The small molecule library studied consisted of 11 synthesized and 3 commercially available molecules representative of bioactive molecules comprising corresponding functional groups (FIG. 4). Their chemical characteristics spanned a wide range of charges (4 negative, 6 neutral, 4 positive), hydrophobicity (−4.3<log P<−1.3), and functional groups (Table 2). For each of the 28 molecule-GO pairs, molecular adsorption, GO sedimentation, and cellular delivery enhancement were measured in 10% serum-supplemented minimum essential media (FIG. 5). From these results, the relative importance of different chemical groups in GO surface interaction and the factors controlling GO delivery performance were assessed.

TABLE 1

GO Size Summary

| Sample | Square root of area (nm) | | Height (nm) | |
|---|---|---|---|---|
| | Mean | Median | Mean | Median |
| 150 nm GO | 179.3 | 144.3 | 0.86 | 0.84 |
| 1500 nm GO | 1676.6 | 999.8 | 0.90 | 0.85 |

TABLE 2

Chemical Characteristics of Gd(III)-labeled Small Molecules

| Molecule | Charge | Hydration Number | Water-Octanol LogP | Hydrogen Bonding Group |
|---|---|---|---|---|
| 1 | 0 | 1 | −2.18 ± 0.02 | |
| 2 | 0 | 1 | −3.98 ± 0.06 | —OH |
| 3 | −1 | 1 | −4.05 ± 0.17 | —OPO$_3$H |
| 4 | −1 | 1 | −3.44 ± 0.28 | —CO$_2$H |
| 5 | +1 | 1 | −4.33 ± 0.46 | |
| 6 | 0 | 1 | −1.26 ± 0.08 | |
| 7 | 0 | 2 | −3.71 ± 0.02 | |
| 8 | +1 | 2 | −3.86 ± 0.01 | —NH$_2$ |

TABLE 2-continued

Chemical Characteristics of Gd(III)-labeled Small Molecules

| Molecule | Charge | Hydration Number | Water-Octanol LogP | Hydrogen Bonding Group |
|---|---|---|---|---|
| 9 | +1 | 2 | −3.98 ± 0.07 | —NH$_2$ |
| 10 | +1 | 2 | −1.63 ± 0.04 | —NH$_2$ |
| 11 | −2 | 1 | −3.80 ± 0.29 | |
| 12 | 0 | 1 | −3.42 ± 0.08 | —NH$_2$ |
| 13 | 0 | 1 | −3.59 ± 0.16 | |
| 14 | −1 | 1 | −3.62 ± 0.23 | |

Errors show SEM

Molecular Adsorption on GO.

Figure 5A:
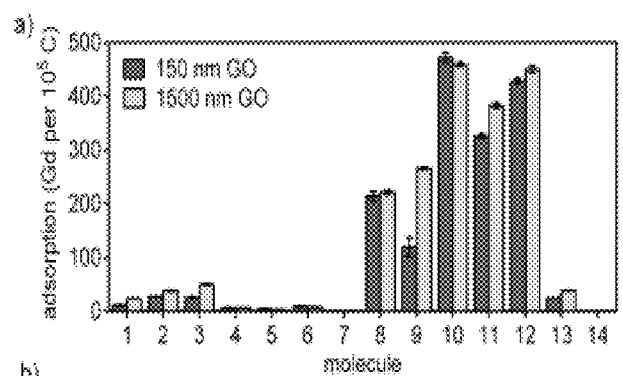
FIGS. 5A-C. A) GO adsorbed a variety of molecules in cell culture media with amines (8, 9, 10, 12) producing the strongest interaction and hydroxyls (2) and phosphates (3) placing a far second. B) GO sedimentation induced by molecular adsorption was measured by the fraction of GO remaining in the supernatant after centrifugation at varying speeds. The area under each curve (AUC) can be used to quantify sedimentation. C) In cell culture, co-incubation with GO enhanced the cellular delivery of a variety of molecules up to 13-fold. The Gd(III) and GO incubation concentrations were 188 µM and 18.8 µg/mL, respectively. Error bars show SEM.

Out of the 14 molecules in the library, 8 showed appreciable adsorption on GO up to a loading ratio of 27 wt % (FIG. 5A). For comparison, reported loading ratios for Camptothecin, Magnevist-PDDA, and Doxorubicin are 5 wt %, 31 wt %, and 131-400 wt %, respectively. The 1500 nm GO exhibited similar to slightly higher adsorption compared to the 150 nm GO, indicating that the molecules interact mainly with the GO basal planes as opposed to their edges.

Molecules with amines (8, 9, 10, and 12) showed the most prominent adsorption, followed by those with hydroxyls (2) and phosphates (3) with a 10-20 fold difference. The strong interaction between amines and GO is consistent with similar observations published for graphenes and carbon nanotubes. This commonality suggests that the sp$^2$ carbon network contributed to the amine-GO interaction in addition to the oxygen groups. Curiously, 6 exhibited one of the lowest adsorptions within the library despite the expected π interactions from its triazole and benzene rings. This result contradicts the prevalent view on cargo-GO interaction but is consistent with the prior DFT studies.

Figure 6A:
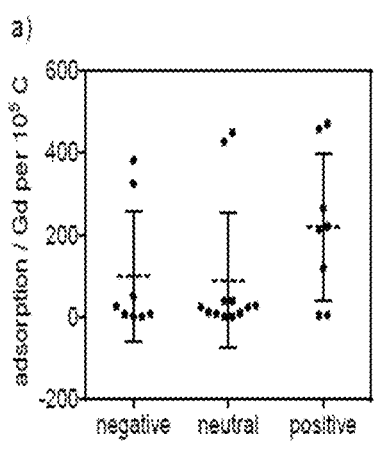
FIGS. 6A-C. Adsorption as a function of A) charge, B) hydrophobicity, and C) hydrogen bonding potential of the adsorbing molecule on GO. No significant correlation was observed between adsorption and any of the chemical variables, indicating that GO adsorption in media cannot be simply predicted by charge interaction, hydrophobicity (for Log P<0), or hydrogen bonding alone. Hydrophobicity was measured by the water-octanol partition coefficient. The hydrogen bonding groups include hydroxyl, phosphate, carboxylic acid, and primary amine. A) and C) combine data from the 150 nm and the 1500 nm GO. Dashed lines in A) and C) show mean. Error bars show SD in A) and C), and SEM in B).
Figure 6B:
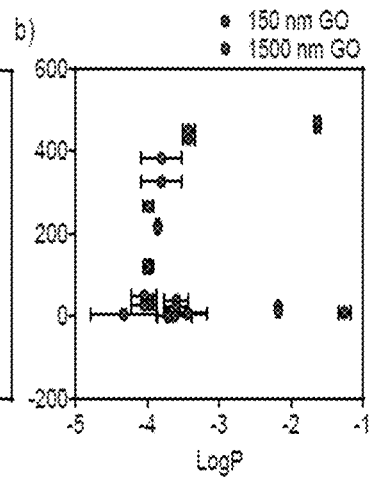
Figure 6C:
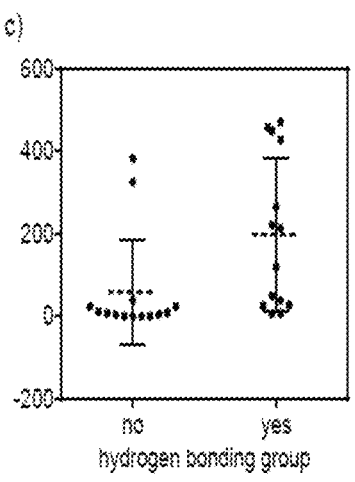

Further quantitative analysis was prompted by the adsorption of Magnevist (11) as the molecule lacks apparently available amines to mediate a strong interaction. The result showed that adsorption could not be easily predicted by the charge, hydrophobicity, or hydrogen bonding potential of the adsorbing molecule (FIG. 6). Therefore, forces outside of the amine-GO interaction contribute to GO adsorption, but their intricacies in complex media are presently beyond prediction by simple chemical variables.

GO Sedimentation.

Surface-adsorbing molecules have the potential to modify the sedimentation behavior of GO by influencing the attractive and repulsive forces between sheets. Sedimentation is generally regarded as an undesirable property of nanomaterials due to the additional variability it introduces into the system. However, the same phenomenon can benefit cellular delivery via a local concentrating effect at the bottom of the cell culture. To investigate this aspect of GO delivery, the GO sedimentation of each molecule-GO pair was measured by recording the percentage of GO remaining in the supernatant after centrifugation at varying speeds (FIG. 5B). Quantitative comparisons were made by a calculation of the area under the sedimentation curve (AUC). The results showed increased sedimentation of the 1500 nm GO compared to the smaller GO, as expected. Additionally, a minimum adsorption of 100 molecules/10$^5$ C was found to be necessary to influence sedimentation, with the degree of impact varying depending on the adsorbing molecule.

Cellular Delivery Enhancement by GO Co-Incubation.

Figure 5C:
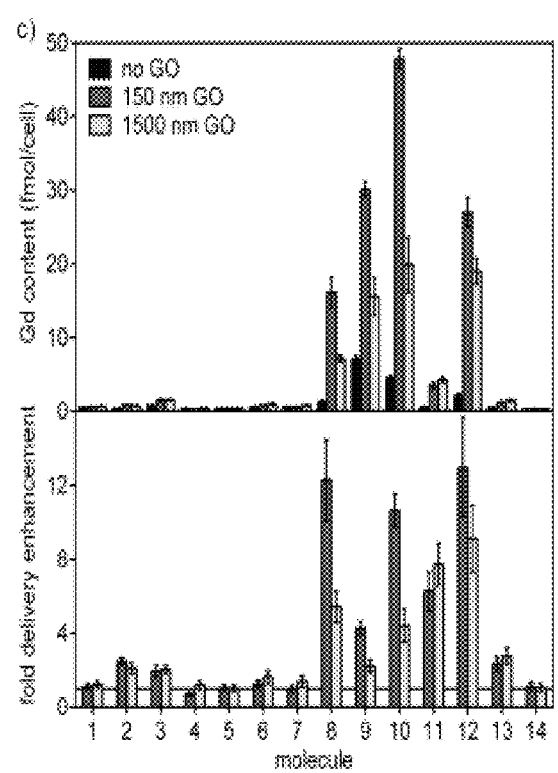
Figure 5B:
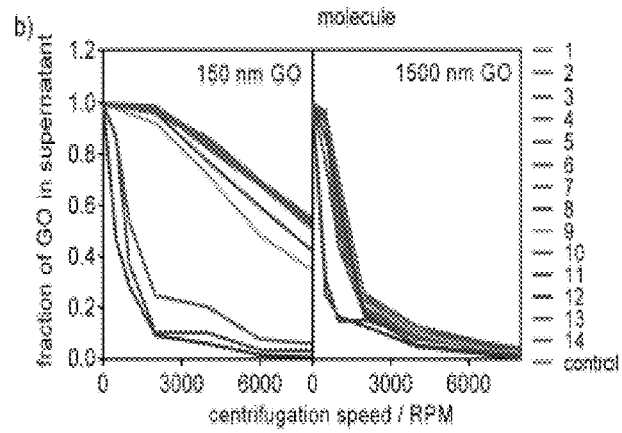
Figure 7A:
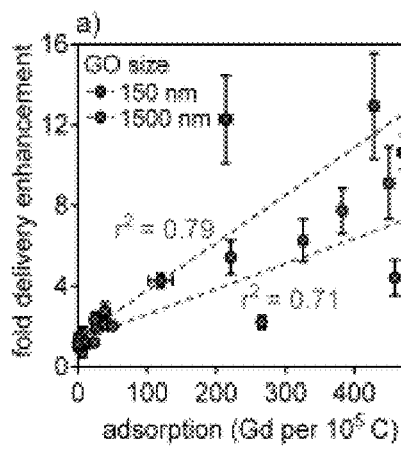
FIGS. 7A-C. Molecular adsorption, GO sedimentation, and GO size control the cellular delivery process. Molecules that A) exhibited higher adsorption and B) induced increased sedimentation experienced greater delivery enhancement by GO. Simple linear regression required separate fits for the two GO sizes. C) Multiple linear regression united the datasets with a model that explained 92% of all observed variances in delivery enhancement. Each of adsorption, sedimentation, and size was found to be significant factors at $p<10-6$. Error bars show SEM.
Figure 7B:
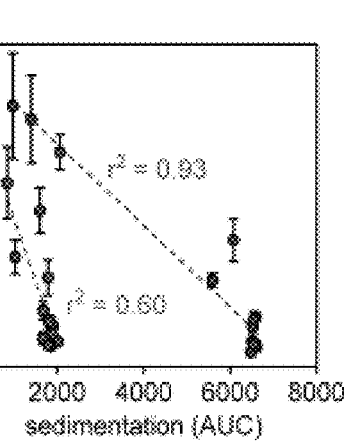

When the library of 14 molecules was co-incubated with GO in cell culture (HeLa), delivery enhancement of up to 13 fold was observed (FIG. 5C, Table 3). Varying degrees of adsorption among the different molecules explain 70-80% of the variances in their delivery enhancement by GO (FIG. 7A). Additionally, molecules that induced GO sedimentation, as indicated by smaller AUC, gained the most in delivery (FIG. 7B).

TABLE 3

Delivery of Gd(III)-labeled Molecules With and Without GO

| Molecule | Gd content (fmol/cell) | | | | | | | | | | Outliers | | | |
|---|---|---|---|---|---|---|---|---|---|---|---|---|---|---|
| 1 | 0.62 | 0.67 | 0.36 | 0.63 | 0.40 | | | | | | | | | |
| +150 nm GO | 0.63 | 0.63 | 0.44 | 0.58 | 0.57 | 0.76 | 0.57 | | | | 1.11 | 1.24 | | |
| +1500 nm GO | 0.59 | 0.58 | 0.39 | 0.77 | 0.86 | 0.76 | 0.64 | | | | 1.18 | 1.45 | | |
| 2 | 0.30 | 0.38 | 0.36 | | | | | | | | | | | |
| +150 nm GO | 0.84 | 0.81 | 0.90 | | | | | | | | | | | |
| +1500 nm GO | 0.59 | 0.88 | 0.70 | | | | | | | | | | | |
| 3 | 0.74 | 0.90 | 0.65 | | | | | | | | | | | |
| +150 nm GO | 1.84 | 1.36 | 1.29 | | | | | | | | | | | |
| +1500 nm GO | 1.61 | 1.64 | 1.41 | | | | | | | | | | | |
| 4 | 0.51 | 0.26 | 0.25 | 0.23 | 0.34 | 0.36 | | | | | 0.76 | | | |
| +150 nm GO | 0.31 | 0.25 | 0.13 | 0.16 | 0.17 | 0.20 | 0.23 | 0.29 | 0.22 | 0.23 | 0.33 | 0.66 | 0.76 | 0.62 |
| +1500 nm GO | 0.58 | 0.27 | 0.33 | 0.30 | 0.31 | 0.53 | | | | | 1.00 | | | |
| 5 | 0.52 | 0.29 | 0.25 | 0.35 | 0.37 | | | | | | | | | |
| +150 nm GO | 0.37 | 0.29 | 0.42 | 0.43 | | | | | | | 2.73 | | | |
| +1500 nm GO | 0.42 | 0.36 | 0.32 | | | | | | | | | | | |
| 6 | 0.78 | 0.72 | 0.40 | 0.47 | 0.58 | | | | | | | | | |
| +150 nm GO | 1.13 | 0.53 | 0.68 | 0.73 | 0.47 | 0.87 | 0.73 | | | | 3.26 | | | |
| +1500 nm GO | 1.29 | 1.24 | 0.67 | 0.64 | | | | | | | 4.12 | | | |
| 7 | 0.47 | 0.39 | 0.51 | 0.46 | 0.75 | 0.83 | | | | | 4.93* | 4.31* | | |
| +150 nm GO | 0.53 | 0.39 | 0.39 | 0.42 | 0.44 | 0.44 | 1.09 | 0.73 | | | 13.51 | 3.25 | | |
| +1500 nm GO | 0.63 | 0.55 | 0.68 | 0.50 | 1.05 | 1.36 | | | | | 6.54 | 4.00 | | |
| 8 | 0.68 | 1.78 | 1.87 | 1.16 | 0.94 | 1.30 | 1.48 | | | | | | | |
| +150 nm GO | 13.40 | 20.22 | 14.84 | | | | | | | | | | | |
| +1500 nm GO | 7.61 | 7.56 | 6.31 | | | | | | | | | | | |
| 9 | 6.86 | 7.54 | 4.78 | 7.33 | 8.77 | 6.65 | 7.40 | | | | 13.02* | 14.46* | 18.05 | 24.04 |
| +150 nm GO | 28.63 | 32.09 | 29.78 | | | | | | | | | | | |
| +1500 nm GO | 11.67 | 20.36 | 14.83 | | | | | | | | | | | |
| 10 | 3.88 | 5.08 | 4.54 | | | | | | | | | | | |
| +150 nm GO | 45.53 | 50.10 | 48.08 | | | | | | | | | | | |
| +1500 nm GO | 14.47 | 26.93 | 18.26 | | | | | | | | | | | |
| 11 | 0.34 | 0.30 | 0.54 | 0.82 | 0.51 | 0.72 | 0.61 | 0.61 | | | | | | |
| +150 nm GO | 2.36 | 2.49 | 4.37 | 4.24 | 5.87 | 2.95 | 2.73 | 2.85 | | | | | | |
| +1500 nm GO | 5.16 | 5.75 | 4.01 | 3.75 | 3.78 | 3.36 | | | | | | | | |
| 12 | 1.99 | 3.84 | 1.83 | 1.26 | 1.04 | 1.29 | 2.63 | 2.80 | | | | | | |
| +150 nm GO | 23.98 | 30.83 | 26.16 | | | | | | | | | | | |
| +1500 nm GO | 24.27 | 20.08 | 13.86 | 16.98 | 19.90 | | | | | | | | | |
| 13 | 0.51 | 0.42 | 0.61 | | | | | | | | | | | |
| +150 nm GO | 1.09 | 1.47 | 1.02 | | | | | | | | | | | |
| +1500 nm GO | 1.36 | 1.84 | 0.82 | 1.59 | 1.47 | | | | | | 0.53* | 0.55* | | |
| 14 | 0.22 | 0.31 | 0.20 | | | | | | | | | | | |
| +150 nm GO | 0.35 | 0.26 | 0.21 | | | | | | | | | | | |
| +1500 nm GO | 0.34 | 0.21 | 0.18 | 0.31 | | | | | | | 4.32 | | | |
| 150 nm GO | 0.08 | 0.01 | | | | | | | | | | | | |
| 1500 nm GO | −0.01 | −0.01 | −0.01 | | | | | | | | | | | |

Outliers were removed using Chauvenet's criterion unless marked.
*removed based on experimenter judgment.

Figure 7C:
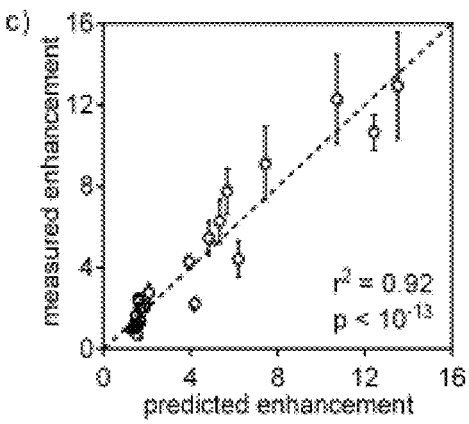
Figure 8:
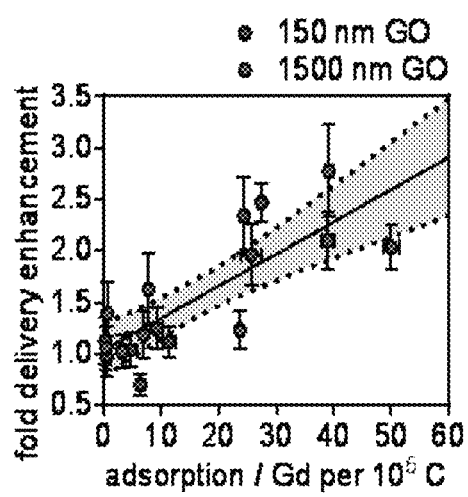
FIG. 8. A significant correlation between delivery enhancement and adsorption can be found for molecules that did not increase GO sedimentation. The correlation was found for both the 150 nm and the 1500 nm GO. Adsorption predicts delivery enhancement independent of size and sedimentation. Error bars show SEM. Gray band shows 95% confidence interval.

Univariate analysis is limited by factor interactions and confounding variables; therefore, multiple linear regression was employed to build a more robust quantitative model. Regression analysis shows that adsorption, sedimentation, and size are all highly significant independent predictors of delivery enhancement (FIGS. 7C, 8, Table 4). The regression coefficients for adsorption ($b_1$), sedimentation ($b_2$), and size ($b_3$) are $1.0 \times 10^{-2}$, $-1.4 \times 10^{-3}$, and $-7.2 \times 10^{-3}$, respectively, when the variables are expressed in units of Gd/$10^5$C, AUC, and nm. The negative sign of $b_3$ indicates that cells intrinsically favor the smaller GO over the larger GO. Importantly, this conclusion was reached after removing the confounding effects of sedimentation. The higher delivery of the smaller GO suggests that it experiences more frequent endocytic uptake and cell membrane insertion relative to the larger GO. The combination of statistical modeling and a quantitative library was proven to be a powerful approach for gaining mechanistic insights into the GO system.

TABLE 4

Multiple Linear Regression Model Coefficients and Statistics

| Predictor | Coefficient ± SEM | p value | VIF |
|---|---|---|---|
| Constant | 11.2 ± 1.1 | | |
| Adsorption (Gd/$10^5$ C) | 1.0 ± 0.1 × $10^{-2}$ | 4.2 × $10^{-7}$ | 1.6 |
| Sedimentation (AUC) | −1.4 ± 0.2 × $10^{-3}$ | 1.8 × $10^{-8}$ | 4.2 |
| Size (nm) | −7.2 ± 0.8 × $10^{-3}$ | 3.6 × $10^{-9}$ | 3.4 |

To further validate GO as the effector of delivery and to better understand the practical parameters that control the process, the co-incubation protocol was studied in more detail on a single cargo-GO combination. Magnevist was selected for the studies because it exhibited high adsorption and is commercially available. The 150 nm GO was selected over the 1500 nm GO due to its superior delivery performance. Co-incubation allowed for the independent control of cargo and GO concentrations in culture, with GO enhancing delivery across two-orders-of-magnitude of Magnevist concentration (0.19-35 mM) (FIG. 9A). Significantly, in the co-incubation approach, it was possible to use a Magnevist concentration that is 100-fold greater compared to using purified Magnevist-GO nanocomplexes reported by our own group and others. Additionally, the cargo-to-GO ratio achievable in co-incubation far exceeds that achievable in a nanocomplex. At 35 mM Magnevist and 20 µg/mL GO, the cargo-to-GO ratio is $2.1 \times 10^6$ Gd/$10^5$ C, compared to the measured adsorption of only 326 Gd/$10^5$ C after repeated washing (FIG. 5A). The substantially higher cargo-to-GO ratio attainable in co-incubation compared to non-covalent conjugation allows weak and transient interactions to contribute to the delivery process. The ability to exploit weak interactions and extremely high cargo concentrations are unique advantages of the co-incubation approach.

In addition to the demonstrated dose-dependent uptake in culture, GO delivery was further validated by two lines of evidence. First, GO coloration can be directly observed in cell pellets after incubation (FIG. 9B). Second, direct addition of Magnevist and GO into media without a pre-incubation period in water eliminated both adsorption and delivery enhancement (FIGS. 9C, 10). The kinetics of GO adsorption and desorption are parameters that can potentially be engineered through the choice of incubation media to further control the delivery process.

Figure 11:
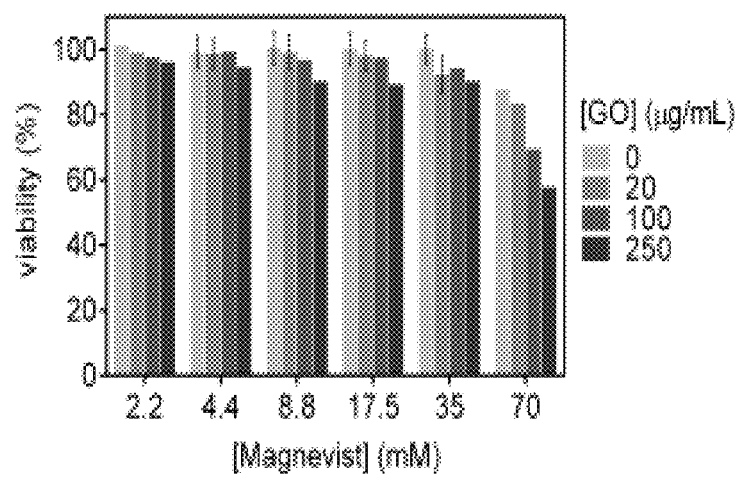
FIG. 11. 24 hour cytotoxicity assay using HeLa cells at increasing Magnevist and GO concentrations. No significant cytotoxicity was observed up to a Magnevist concentration of 35 mM and a GO concentration of 250 µg/mL. The maximum GO dose required for cellular delivery enhancement is 20 µg/mL, or an order of magnitude below the highest test dose. The 150 nm GO was used for the study.
Figure 12A:
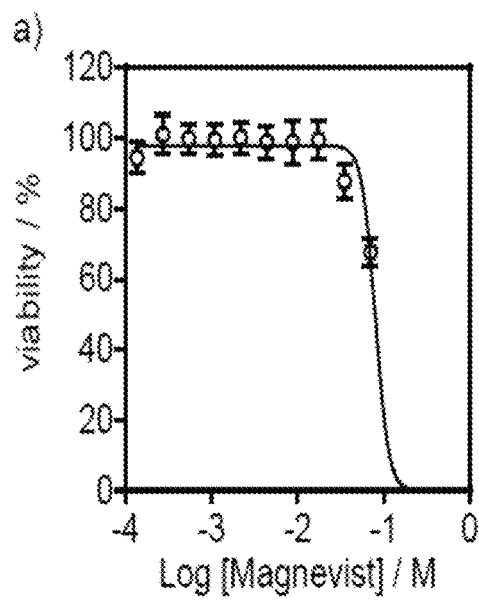
FIGS. 12A-B. Cytotoxicity of Magnevist. A) Viability of HeLa cells at increasing Magnevist concentration as measured by the Guava ViaCount Assay. Analysis includes floating cells at the end of the 24-hr incubation period. The fitted IC50 was 80 mM. B) Same as in a) except analysis was performed after in-plate washing by PBS and does not include floating cells. The IC50 found was 99 mM, comparable to the result obtained in a). The Hill slope was found in B) and fixed in A) to keep the two fits comparable. Fitting was performed using GraphPad Prism software. All incubations were performed for 24 hours. Error bars show SD.
Figure 12B:
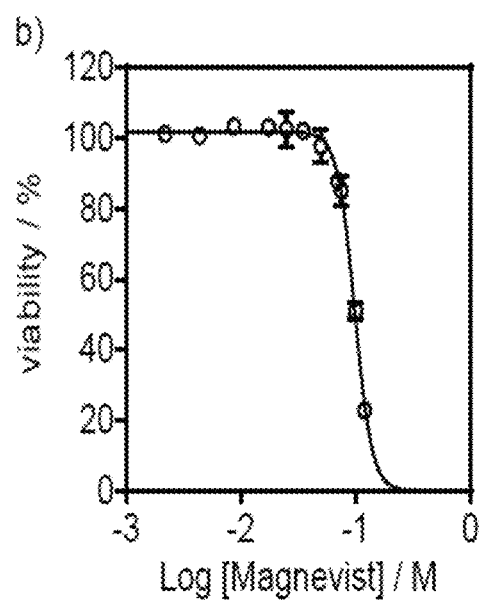

Next, the cytotoxicity of GO was evaluated at varying cargo concentrations on HeLa cells. Cell viability remained above 90% for GO concentrations up to 250 µg/mL and Magnevist concentrations up to 35 mM (FIGS. 11, 12). When Magnevist concentration was increased to 70 mM, synergistic cytotoxicity was observed. However, concentrations as high as 70 mM Magnevist and 250 µg/mL GO were required to decrease the cell viability to below 60%. The high tolerance of cells towards GO is consistent with literature reports and has been shown to be mediated by serum proteins. Based on these results, there is no cytotoxicity concern for GO at the doses and timescales required to achieve delivery enhancement.

Figure 13:
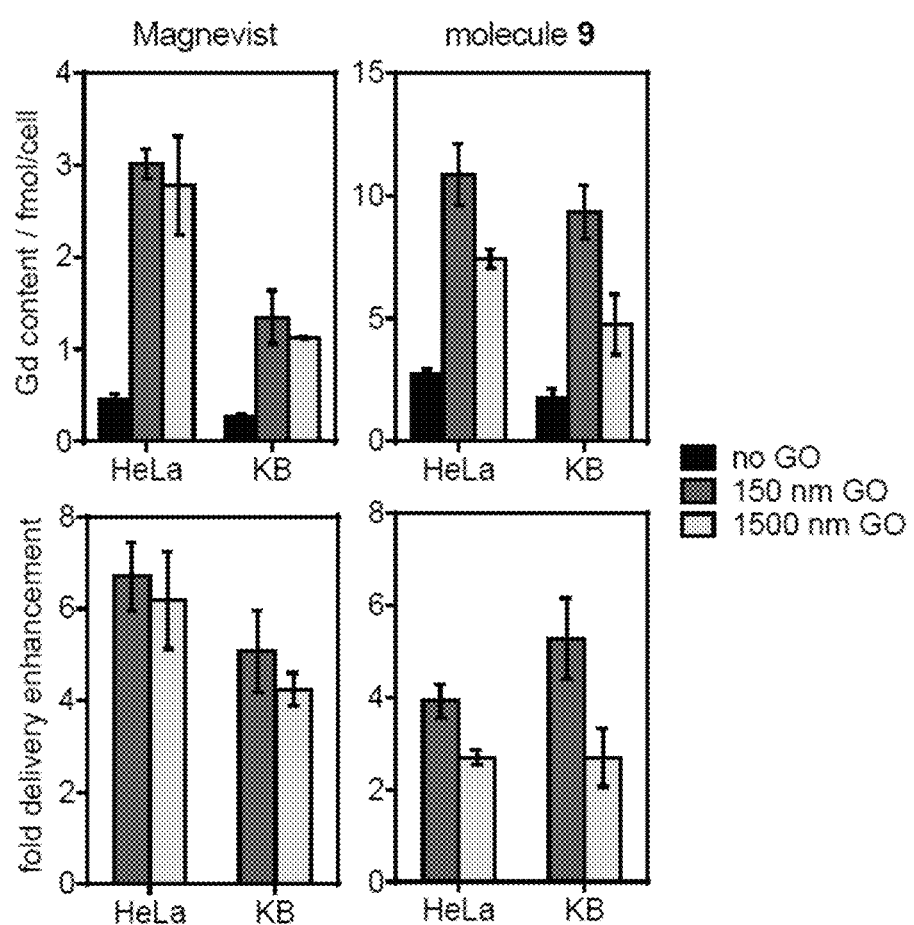
FIG. 13. The generalizability of GO co-incubation as a strategy to enhance cellular delivery was demonstrated in the KB cell line. Similar levels of delivery enhancement were achieved in KB compared to HeLa. This result generalized across 9 and Magnevist (11) for both the 150 nm and the 1500 nm GO. Experiments were performed with 188 µM Gd(III) concentration and 18.8 µg/mL GO incubation concentration. Error bars show SD for Gd content and SEM for delivery enhancement.
Figure 14A:
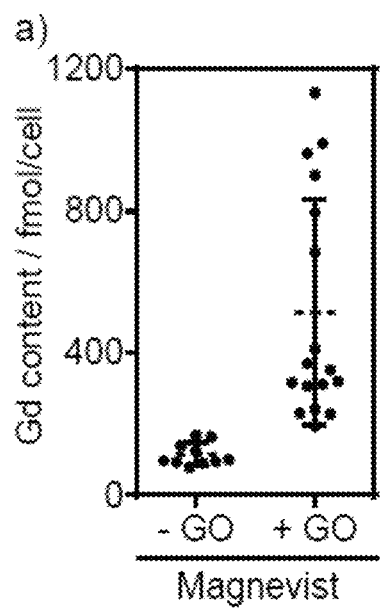
FIGS. 14A-B. Inherent variability in cell delivery by GO co-incubation. A) Magnevist cell labeling with and without GO (150 nm) resulted in % CVs of 62% over 17 trials and 28% over 10 trials, respectively. B) A % CV of 23% was measured across 3 batches of 100-150 nm GO in the delivery of 9. The intra-batch % CV averaged to 33%. Batch 3 was used for all other studies. Experiments in a) were performed with 35 mM Gd(III) concentration and 20 µg/mL GO incubation concentration. Experiments in B) were performed with 188 µM Gd(III) concentration and 18.8 µg/mL GO incubation concentration. Dashed lines in a) show mean. Error bars show SD in A) and SEM in B).
Figure 14B:
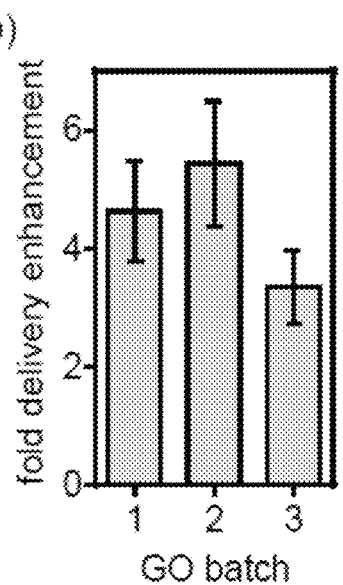
Figure 15A:
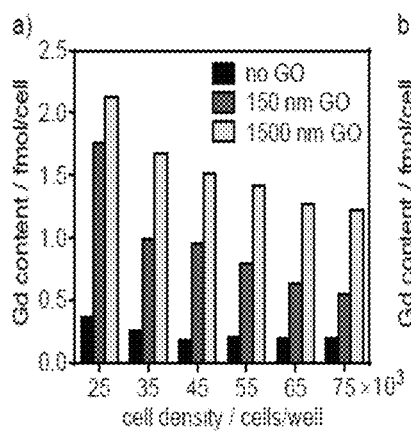
FIGS. 15A-D. Sensitivity of the GO co-incubation protocol to procedural parameters. A) Cellular uptake of Magnevist with and without GO co-incubation decreases with cell density. B) Cellular Gd content decreases when incubating in a 6-well plate compared to a 24-well plate. C) 30% 40% of the cellular Gd content is retained upon washing by centrifugation. The portion washed away is attributed to membrane binding. D) Delivery enhancement achieved by GO (150 nm) co-incubation decreases above 20 µg/mL. Experiment in a) was performed in a 24 well plate at 188 µM Gd(III) concentration and 18.8 µg/mL GO concentration. Experiments in B) and C) were performed at 35 mM Gd(III) concentration and 20 µg/mL GO (150 nm) concentration. Error bars show SD.
Figure 15B:
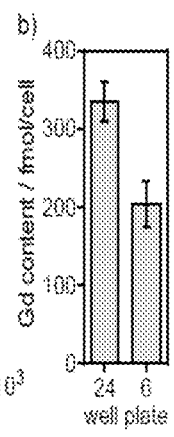
Figure 15C:
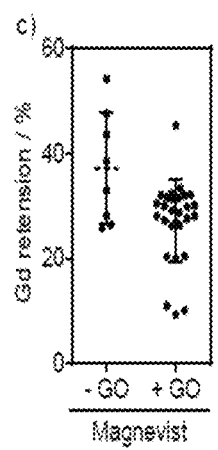
Figure 15D:
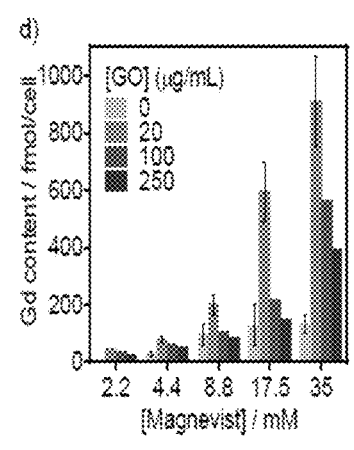

Finally, the robustness of the co-incubation protocol was evaluated in terms of generalizability to other cell lines, inherent variability, and sensitivity to procedural parameters (FIGS. 13-15). GO co-incubation was shown to consistently enhance cellular delivery across the entire range of tested conditions, although the degree of enhancement achieved varied. Parameters such as plated cell density, incubation vessel, and GO concentration influence the performance of GO delivery.

Evaluation of GO Co-Incubation in Gd(III) Cellular MRI.

In addition to serving as a quantitative label, the contrast-enhancing properties of Gd(III) in MRI provides a convenient application for comparing GO co-incubation with the nanoconjugation approach. In cellular MRI, the sensitivity for Gd(III)-labeled cells is directly related to the Gd(III) label relaxivity and the cellular Gd(III) content, with the minimum requirement being 0.1-1 fmol/cell. The highest cellular labeling reported to date is 31 fmol Gd/cell using the clinical agent ProHance at an incubation concentration of 100 mM. Gd(III) agents attached to nanomaterial scaffolds are an attractive alternative because they exhibit increased relaxivity and show efficient cell labeling. However, their incubation concentration is typically limited to the µM range due to colloidal instability or increased toxicity compared to clinical agents. Consequently, typical cellular labeling achieved with nanomaterial agents ranges from 0.1 to 2 fmol Gd/cell, or approximately an order of magnitude below the state-of-the-art. GO co-incubation combines the relaxivity and delivery advantages of nanomaterials with the ability to use extremely high label incubation concentrations.

Figure 16:
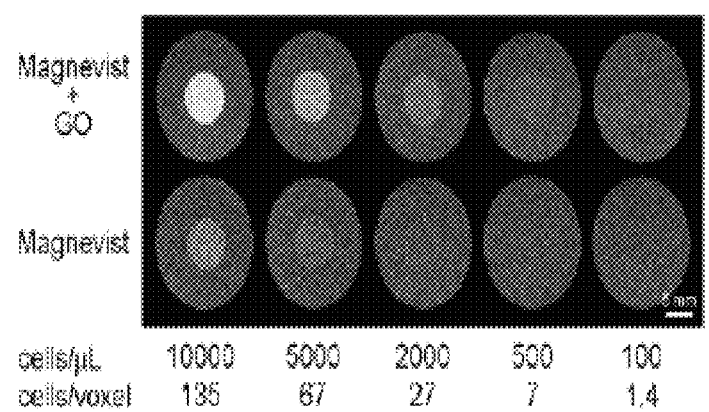
FIG. 16. GO co-incubation enhanced (digital images) the sensitivity of Magnevist-labeled cells from 5000 cells/µL to 500 cells/µL on T1-weighted Mill at 7T. For comparison, a packed cell pellet has approximately 385,000 cells/µL using the reported HeLa cellular volume of 2.6 pL. The 150 nm GO was used for the study.

HeLa cells labeled by Magnevist with and without GO were suspended in agarose at various densities to characterize their sensitivity on MRI (FIG. 16). Procedural changes needed to produce the cell-agarose phantoms, including a change in culturing plates and the need to centrifuge cells, decreased the cellular Gd(III) contents in this experiment compared to the other studies performed (FIGS. 14-15). The labeling achieved using Magnevist alone (35 mM) and with GO co-incubation (10 µg/mL) was 30 and 47 fmol Gd/cell, respectively. As expected, the labeling by Magnevist was comparable to the highest reported literature value, while that attained with GO represented a further improvement of 57%. Compared to Gd(III)-DNA gold nanoparticles, Gd(III)-labeled polymer-liposomes, gadonanotubes, and gadofullerenols, GO co-incubation achieved a cellular Gd(III) payload that is 30-50 fold greater. The co-incubation approach provided an advantage in Gd(III) delivery over nanoconjugation by allowing the use mM cargo concentrations during incubation.

In addition to Gd(III) payload, the sensitivity of cellular MRI is affected by Gd(III) relaxivity. Relaxivity is a measure of the ability of a paramagnetic label to generate contrast. GO has been known to increase the relaxivity of Gd(III) agents through a slowing of molecular tumbling. Additionally, studies suggest that GO interact with cells by both endocytosis and direct membrane insertion, resulting in the delivery of cargos to the cytosol, the cell membrane, and the endosomes. Therefore, the Gd(III) labels delivered by GO are not expected to experience significant barriers to water access. In contrast, Gd(III) labels without nanomaterial delivery are sequestered into cells by pinocytosis and experience a phenomenon known as relaxivity quenching due to reduced water exchange. The combination of increased Gd(III) payload and enhanced relaxivity mediated by GO has a multiplicative effect that evidently increased the MM sensitivity for labeled cells by nearly 10 fold compared to Magnevist alone (FIG. 16). This level of sensitivity is believed to have not been previously reported for a Gd(III)-nanomaterial and serves as a testament to the advantages of GO co-incubation over nanoconjugation as an approach to nanomaterial delivery.

EXAMPLES OF THE INVENTION

The following non-limiting examples and data illustrate various aspects and features relating to the compositions and/or methods of the present invention, including the use of unmodified graphene oxide for the cellular delivery of hydrophilic small molecules. In comparison with the prior art, the present methods and compositions provide results and data which are surprising, unexpected and contrary thereto. While the utility of this invention is illustrated through the use of several unmodified graphene oxide embodiments and hydrophilic molecular components which can be used therewith, it will be understood by those skilled in the art that comparable results are obtainable with various other graphene oxide embodiments and other small molecule therapeutic agents, as are commensurate with the scope of this invention.

Example 1

Synthesis of Gd(III)-Labeled Molecules.

All reactions were conducted under an atmosphere of nitrogen gas and all solvents and chemical reagents were obtained from Sigma-Aldrich Chemical Company (St. Louis, Mo.) unless otherwise noted and used without further purification. Deionized water (18.2 MΩ·cm at 25° C.) was obtained from a Millipore Q-Guard System equipped with a quantum Ex cartridge. Thin-layer chromatography (TLC) was performed using 60F 254 silica gel plates (EMD Biosciences) and flash column chromatography was performed with standard grade 60 Å 230-400 mesh silica gel (Sorbent Technologies).

Purification and characterization were performed using reverse phase HPLC/MS. Electrospray ionization mass spectrometry (ESI-MS) spectra were acquired on a Varian 1200L single-quadrupole mass spectrometer. Unless otherwise noted, analytical reverse-phase HPLC-MS was performed on a Varian Prostar 500 system with a Waters 4.6×250 mm 5 μm Atlantis C18 column and preparative runs were performed on a Waters 19×250 mm Atlantis C18 Column. Mobile phases consisted of deionized water (Solvent A) and HPLC-grade acetonitrile (Solvent B). Where applicable, a Waters 4.6×150 mm X-Bridge analytical C18 5 μm column and the corresponding semi-preparative equivalent, 19×150 mm were used. Solvents used with this column consisted of aqueous ammonium hydroxide, pH=10.37 (Solvent C) and HPLC grade acetonitrile (Solvent D).

Synthesis of 1-6 were carried out via copper(I)-catalyzed azide-alkyne click chemistry between Gd(HPN₃DO3A) and the corresponding alkyne-functionalized pendant group. Gd(HPN₃DO3A) is an azide-bearing Gd(III) chelate synthesized using previously published procedures. 7 was synthesized following previously published procedures. 8-10 were synthesized following a synthetic route reported in the literature with modifications. 11 was purchased from Sigma-Aldrich (Catalogue number 381667) and used as supplied. When preparing solutions of 11, the pH was adjusted to 7 using 2.0M NaOH. 12 was synthesized following previously published procedures. 13 was synthesized by reacting DO3A with propylene oxide, followed by metalation with Gd(OAc)₃. 14 was generated by metalating the DOTA ligand purchased from Macrocyclics, Inc. Details of the reaction conditions and purification methods are reported below.

Tris-Hydroxypropyl Triazolyl Amine (THPTA) and Tris-Benzyl Triazolyl Amine (TBTA) used as stabilizing and solubilizing ligands for copper(I) during click reactions were synthesized and purified according to literature procedure. (Hong, V.; Presolski, S. I.; Ma, C.; Finn, M. G. Analysis and Optimization of Copper-Catalyzed Azide-Alkyne Cycloaddition for Bioconjugation. *Angew. Chem. Int. Ed.* 2009, 48, 9879-9883; Chan, T. R.; Hilgraf, R.; Sharpless, K. B.; Fokin, V. V. Polytriazoles as Copper(I)-Stabilizing Ligands in Catalysis. *Org. Lett.* 2004, 6, 2853-2855.) Gd(HPN₃DO3A) used in the synthesis of 1-6 was synthesized using previously published procedures. (Mastarone, D. J.; Harrison, V. S. R.; Eckermann, A. L.; Parigi, G.; Luchinat, C.; Meade, T. J. A Modular System for the Synthesis of Multiplexed Magnetic Resonance Probes. *J. Am. Chem. Soc.* 2011, 133, 5329-5337.) 1,4,7-(Tris-tert-butyl acetate)-1,4,7,10-tetraazacyclodecane.HBr (tert-butyl DO3A) used in the synthesis of 7-10 was synthesized as previously described. (Axelsson, O.; Olsson, A. Synthesis of Cyclen Derivatives. WO/2006/112723, 2006.)

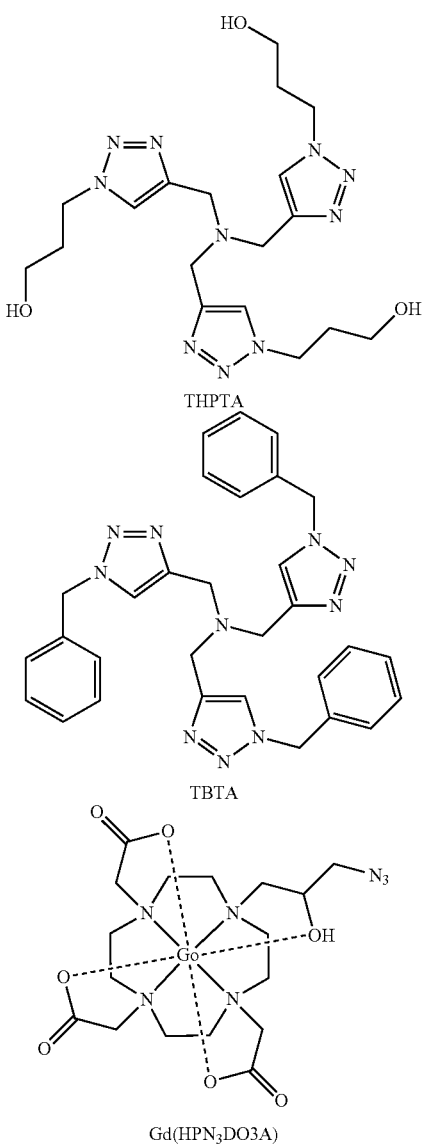

THPTA

TBTA

Gd(HPN₃DO3A)

Example 1a

Synthesis of 1

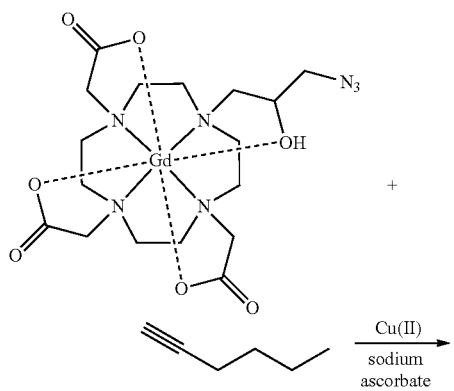

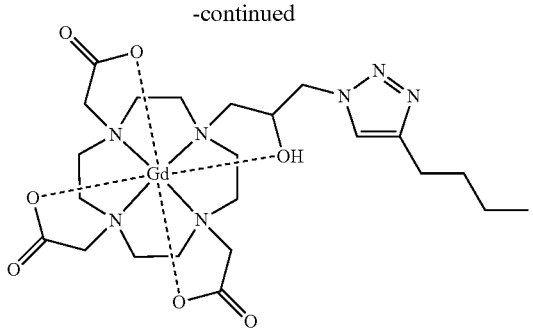

To a 250 mL round bottom flask was added water (25 mL), [Gd(HPN₃DO3A)(H₂O)] (0.150 g, 0.25 mmol) and Cu(II)SO₄.5H₂O (0.006 g, 0.025 mmol). To the stirring mixture was added tetrahydrofuran (24 mL). To a 2 mL glass vial was added tetrahydrofuran (1 mL), 1-hexyne (0.041 g, 0.50 mmol), and tris-benzyltriazolylamine (0.016 g, 0.03 mmol). The tetrahydrofuran containing the dissolved 1-hexyne and TBTA was then added to the stirring mixture of [Gd(HPN₃DO3A)(H₂O)] and Cu(II)SO₄.5H₂O. To this was added sodium ascorbate (0.05 g, 0.25 mmol) and the mixture was left to stir under nitrogen overnight at room temperature. The crude mixture was purified by semi-preparative reverse phase HPLC using the following conditions: 0-5 min 0% solvent B, 20 min 40% solvent B, 25 min 100% solvent B, 25-30 min 0% solvent B, 35 min 0% Solvent B and 35-40 min 0% solvent B. The desired product elutes from 20.6 to 21.8 minutes as monitored by UV-vis at 201/210 nm and was collected and lyophilized. Yield: 0.121 g (71%). (m/z): observed: 681.3, calculated: 681.8 [M+H]₊.

Example 1b

Synthesis of 2

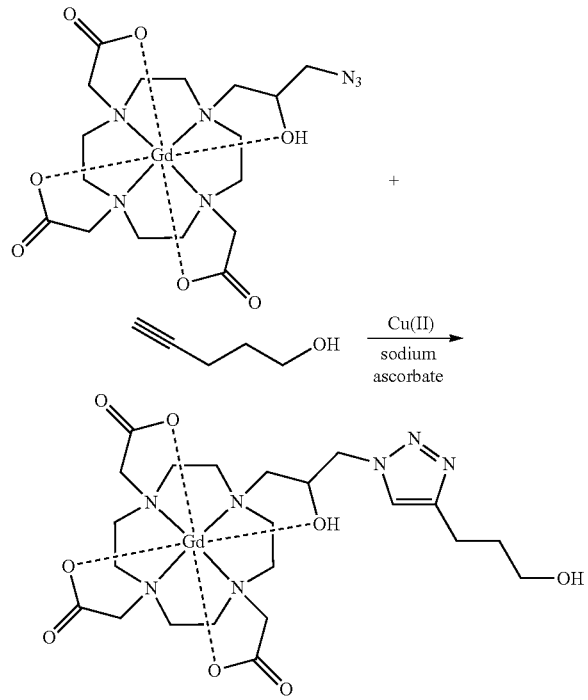

To a 250 mL round bottom flask was added water (75 mL) and [Gd(HPN₃DO3A)(H₂O)] (0.150 g, 0.25 mmol), Cu(II)SO₄.5H₂O (0.006 g, 0.025 mmol) and tris-hydroxypropyl-triazolylamine (0.013 g, 0.03 mmol). With dissolution of these components was then added tert-butanol (24 mL). To a separate, 2 mL glass vial was added tert-butanol (1 mL) and 4-pentyne-1-ol (0.042 g, 0.50 mmol). To the stirring solution of [Gd(HPN₃DO 3A)(H₂O)], Cu(II) and THPTA was added the solution of 4-pentyn-1-ol in tert-butanol. To this was further added sodium ascorbate (0.05 g, 0.25 mmol) and the mixture was left to stir under nitrogen overnight at room temperature. The crude mixture was purified by semi-preparative reverse phase HPLC using the following conditions: 0-5 min 0% solvent B, 20 min 40% solvent B, 25 min 100% solvent B, 25-30 min 0% solvent B, 35 min 0% Solvent B and 35-40 min 0% solvent B. The desired product elutes from 16.4 to 16.8 minutes as monitored by UV-vis at 201/210 nm and was collected and lyophilized. Yield: 0.125 g (73%). (m/z): observed: 683.1, calculated: 683.8 [M+H]⁺.

Example 1c

Synthesis of 3

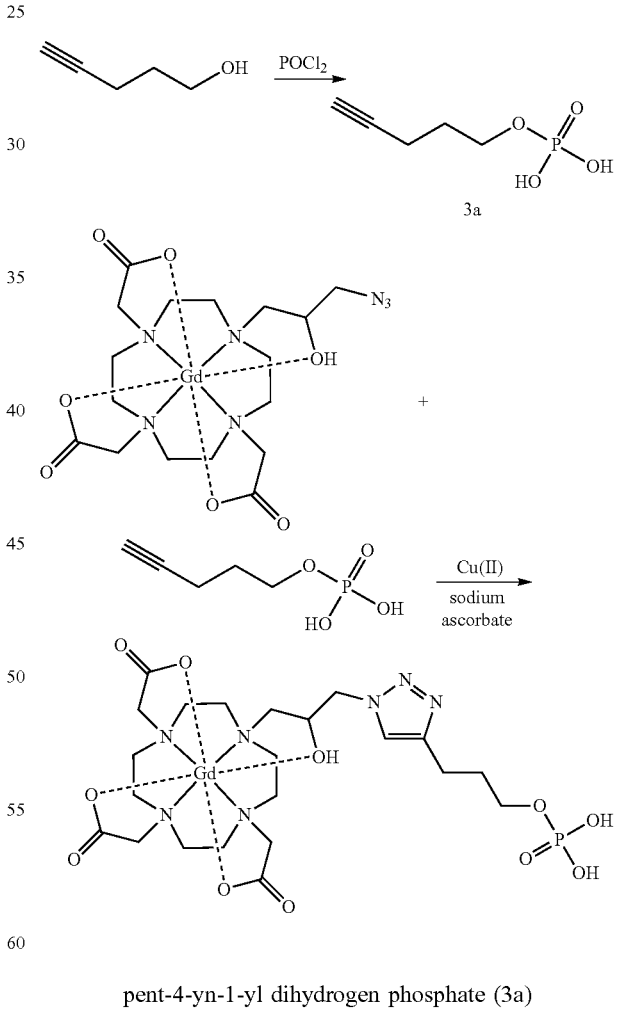

pent-4-yn-1-yl dihydrogen phosphate (3a)

To an oven-dried 50 mL round bottom flask was added a magnetic stir bar and anhydrous diethyl ether (25 mL). To the stirring solvent was added 4-pentyne-1-ol (0.452 g, 6.57 mmol), triethylamine (0.665 g, 6.57 mmol), and pyridine (1.039 g, 13.14 mmol). To a second, oven-dried 100 mL round bottom flask was added anhydrous diethyl ether (25 mL) and phosphorous oxychloride (1.211 g, 7.90 mmol). The flask containing phosphorous oxychloride was cooled to 0° C. with stirring, at which time was added dropwise the solution of 4-pentyne-1-ol over two hours, whereupon the mixture became cloudy with a visible white suspension. After the complete addition of 4-pentyne-1-ol solution, the reaction mixture was allowed to warm to room temperature and remain stirring for a further 12 hours. The pale brown mixture was then cooled again to 0° C. open to the atmosphere, and water (5 mL) was added and the reaction left to stir for one hour. To the stirring biphasic mixture was added 10 mL of 1M NaOH (aq), followed by separation of the organic phase using a separatory funnel and further extraction of the aqueous layer using additional diethyl ether (2×10 mL). To the isolated aqueous mixture was then added 15 mL of 1M HCl (aq), followed by extraction with ethyl acetate (3×10 mL). Successful synthesis and isolation of the product in the ethyl acetate was confirmed by ESI-MS of the phosphorylated product (m/z): observed: 162.8, calculated: 163.1 [M−H]⁻. The crude product was taken forward without further purification.

Gd(HPN₃DO3A)-phosphate (3)

To a 250 mL round bottom flask was added 0.5 M triethylammonium acetate buffer pH 7.0 (100 mL), [Gd(HPN₃DO 3A)(H₂O)] (0.150 g, 0.25 mmol), Cu(II)SO₄.5H₂O (0.006 g, 0.025 mmol), tris-hydroxypropyltriazolylamine (0.013 g, 0.03 mmol), and 3a (unpurified, approximately 6.0 mmol). To this was further added sodium ascorbate (0.05 g, 0.25 mmol) and the mixture was left to stir overnight under nitrogen at room temperature. The crude mixture was purified by semipreparative reverse phase HPLC using the following conditions: 0-5 min 0% solvent B, 20 min 40% solvent B, 25 min 100% solvent B, 25-30 min 0% solvent B, 35 min 0% Solvent B and 35-40 min 0% solvent B. The desired product elutes from 10.4 to 12.5 minutes as monitored by UV-vis at 201/210 nm and was collected and lyophilized. Yield: 0.095 g (54%). (m/z): observed: 763.3, calculated: 763.8 [M+H]⁺.

Example 1d

Synthesis of 4

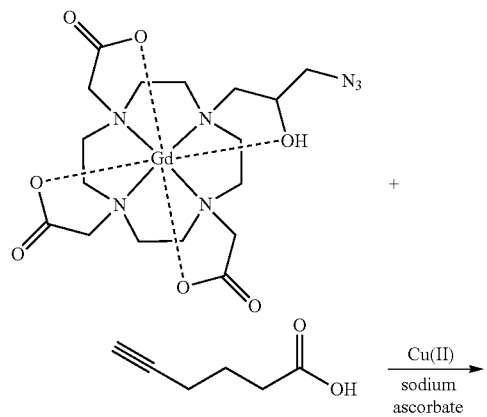

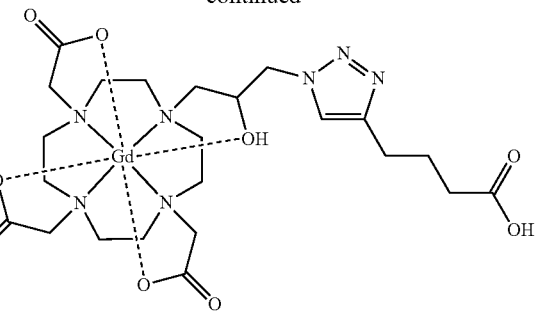

To a 250 mL round bottom flask was added water (100 mL) and [Gd(HPN₃DO 3A)(H₂O)] (0.150 g, 0.25 mmol), Cu(II)SO₄.5H₂O (0.006 g, 0.025 mmol), tris-hydroxypropyltriazolylamine (0.013 g, 0.03 mmol) and 5-hexynoic acid (0.056 g, 0.50 mmol). To this was further added sodium ascorbate (0.05 g, 0.25 mmol) and the mixture was left to stir under nitrogen overnight at room temperature. The crude mixture was purified by semipreparative reverse phase HPLC using the following conditions: 0-5 min 0% solvent B, 20 min 40% solvent B, 25 min 100% solvent B, 25-30 min 0% solvent B, 35 min 0% Solvent B and 35-40 min 0% solvent B. The desired product elutes from 10.2 to 11.3 minutes as monitored by UV-vis at 201/210 nm and was collected and lyophilized. Yield: 0.095 g (54%). (m/z): observed: 711.1, calculated: 711.8 [M+H]⁺.

Example 1e

Synthesis of 5

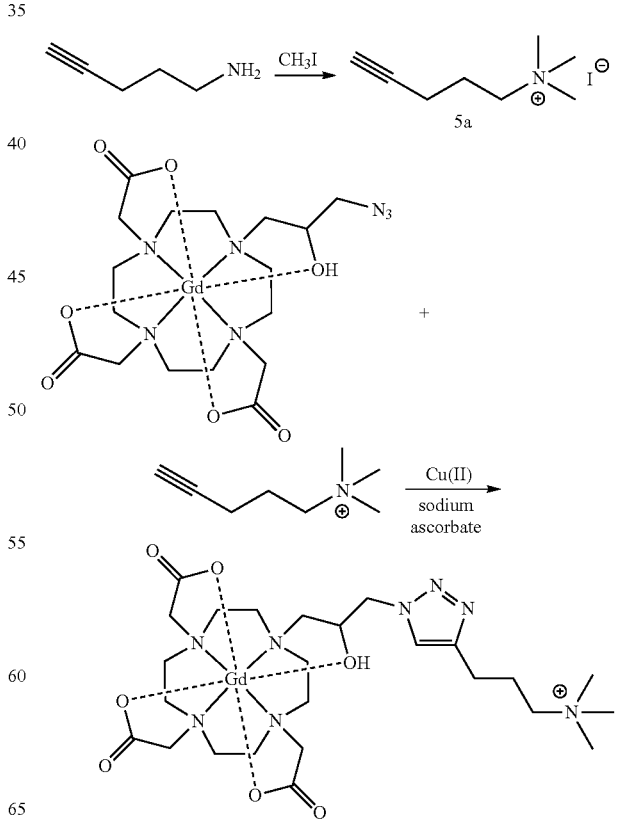

N,N,N-trimethylpent-4-yn-1-ammonium Iodide (5a)

To a dried 10 mL round bottom flask was added a magnetic stir bar, and anhydrous acetonitrile (5 mL). Potassium carbonate (0.500 g, 3.6 mmol) and 4-pentyn-1-amine (0.075 g, 0.90 mmol) were further added. To the stirring mixture containing some visible, insoluble potassium carbonate was added methyl iodide (0.460 g, 3.24 mmol). The reaction was stirred for 12 hours at room temperature. After such time, the reaction was filtered, and evaporated yielding a mixture of the pale yellow solid of the tetra-alkyl iodide product and potassium carbonate. Full conversion of starting material to product was confirmed by ESI-MS. (m/z): observed: 126.4, calculated: 126.2 [M]$^+$. The solid, crude product was taken forward without further purification.

Gd(HPN$_3$DO3A)-tertiary amine (5)

To a 250 mL round bottom flask was added water (75 mL) and [Gd(HPN$_3$DO 3A)(H$_2$O)] (0.150 g, 0.25 mmol), Cu(II)SO$_4$.5H$_2$O (0.006 g, 0.025 mmol) and tris-hydroxypropyl-triazolylamine (0.013 g, 0.03 mmol). After dissolution of these components was then added tert-butanol (25 mL). To a separate, 2 mL glass vial was added 1:1 tert-butanol:water (1 mL) and compound 5a (unpurified, approximately 0.9 mmol). To the stirring solution of [Gd(HPN$_3$DO3A)(H$_2$O)], Cu(II) and THPTA was added the solution of 4-pentyn-1-ol in the tert-butanol water mixture. To this was further added sodium ascorbate (0.05 g, 0.25 mmol) and the mixture was left to stir under nitrogen overnight at room temperature. The crude mixture was purified by semipreparative reverse phase HPLC using the following conditions and solvents C and D: 0-5 min 5% solvent C, 20 min 40% solvent C, 25 min 100% solvent C, 25-30 min 0% solvent C, 35 min 0% Solvent C and 35-40 min 5% solvent C. The desired product elutes from 4.7 to 6.3 minutes as monitored by UV-vis at 201/210 nm and was collected and lyophilized. Yield: 0.125 g (73%). (m/z): observed: 725.0, calculated: 724.9 [M+H]$^-$.

Example 1f

Synthesis of 6

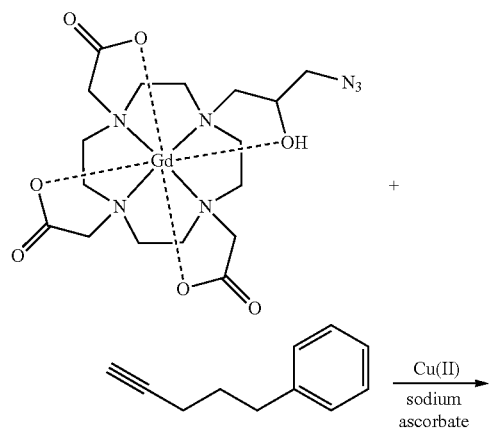

-continued

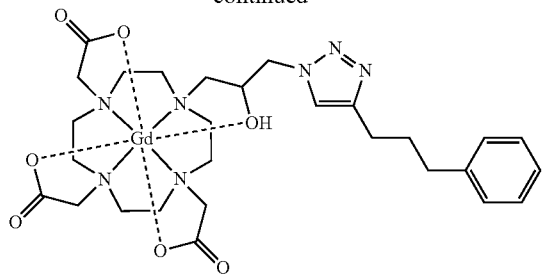

To a 250 mL round bottom flask was added water (25 mL), [Gd(HPN$_3$DO3A)(H$_2$O)] (0.150 g, 0.25 mmol) and Cu(II)SO$_4$.5H$_2$O (0.006 g, 0.025 mmol). To the stirring mixture was added tetrahydrofuran (24 mL). To a 2 mL glass vial was added tetrahydrofuran (1 mL), 5-phenyl-1-pentyne (0.072 g, 0.50 mmol), and tris-hydroxybenzyltriazolylamine (0.016 g, 0.03 mmol). The tetrahydrofuran containing the dissolved 5-phenyl-1-pentyne and TBTA was then added to the stirring mixture of [Gd(HPN$_3$DO3A)(H$_2$O)] and Cu(II)SO$_4$.5H$_2$O. To this was added sodium ascorbate (0.05 g, 0.25 mmol) and the mixture was left to stir under nitrogen overnight at room temperature. The crude mixture was purified by semipreparative reverse phase HPLC using the following conditions: 0-5 min 0% solvent B, 20 min 40% solvent B, 25 min 100% solvent B, 25-30 min 0% solvent B, 35 min 0% Solvent B and 35-40 min 0% solvent B. The desired product elutes from 25.4 to 26.4 minutes as monitored by UV-vis at 201/210 nm and was collected and lyophilized. Yield: 0.156 g (84%). (m/z): observed: 742.4, calculated: 743.9 [M+H]$^+$.

Example 1g

Synthesis of 7

DO3A-tris-tert-butyl ester.HBr was synthesized according to previously published procedures. An aqueous trifluoroacetic acid (TFA) solution, 30:1:1 (TFA:triethylsilane:H$_2$O) was added and stirred at room temperature overnight to deprotect the ligand. TFA was removed from the solution by purging with a stream of nitrogen and concentrating from water twice. 1 equivalent of Gd(CH$_2$COO)$_3$.xH$_2$O was added and the pH of the solution adjusted with 1M NaOH and 1M HCl to 6.5. The resultant was stirred at 60° C. overnight. The crude mixture was purified by semipreparative reverse phase HPLC.

Example 1h

Synthesis of 8

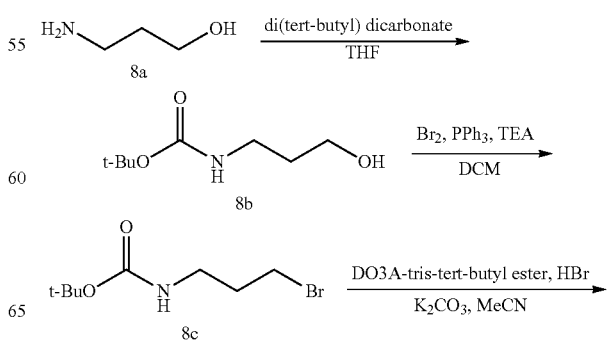

19

-continued

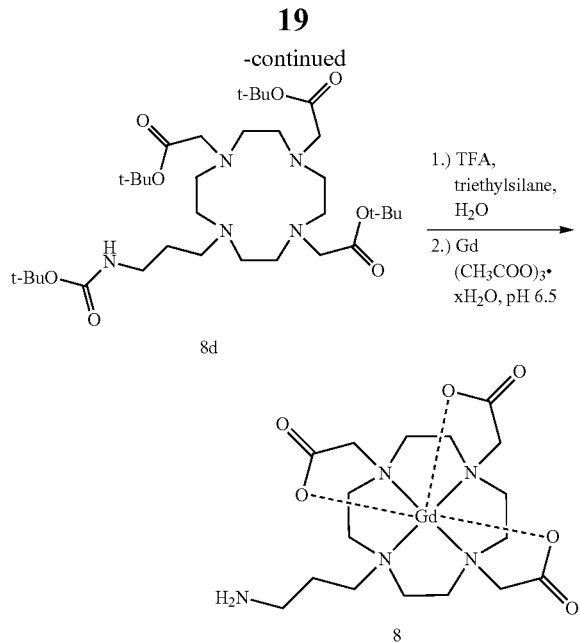

8d

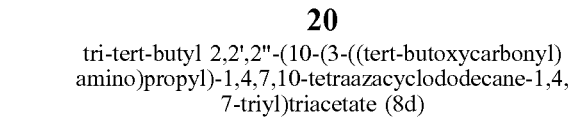

8

N-(tert-butoxycarbonyl)-3-hydroxypropylamine (8b)

Di-tert-butyl dicarbonate (3.046 g, 13.9 mmol) was dissolved in 50 mL of tetrahydrofuran (THF). 3-amino propanol (8a, 1.062 mL, 13.9 mmol) suspended in 50 mL of THF was then added and the reaction stirred at room temperature overnight. The reaction mixture was concentrated under reduced pressure and the crude material purified by flash column chromatography over silica gel with 1:9 methanol:dichloromethane (MeOH:DCM) to afford a pale yellow oil (2.425 g, 99%). $^1$H NMR (500 MHz, CDCl$_3$): δ 4.86 (bs, 1H), 3.66 (m, 2H), 3.29 (quar, 2H, J=6.4, 6.0), 3.19 (bs, 1H), 1.67 (quin, 2H, J=6.0), 1.45 (s, 9H). $^{13}$C NMR (126 MHz, CDCl$_3$): 157.26, 79.71, 59.14, 36.82, 32.87, 28.36.

N-(tert-butoxycarbonyl)-3-bromopropylamine (8c)

Triphenylphosphine (1.553 g, 5.9 mmol) was dissolved in 30 mL of dichloromethane and cooled to 0° C. Triethylamine (0.830 mL, 5.9 mmol) was added via syringe. Bromine (0.305 mL, 5.9 mmol) diluted in 20 mL of DCM was added via syringe and the reaction vessel stirred at 0° C. for 1 hr. Upon warming to room temperature, 8b (0.852 g, 5.4 mmol) suspended in 10 mL of DCM was added via syringe. The reaction mixture was stirred at room temperature overnight. Upon concentration under reduced pressure, the crude reaction was purified by flash column chromatography over silica gel with 1:5 ethyl acetate/hexanes (EtOAc:Hex) to give a yellow oil (0.713 g, 3.2 mmol, 60%). $^1$H NMR (500 MHz, CDCl$_3$): δ 4.69 (bs, 1H), 3.45 (t, 2H), 3.27 (quar, 2H), 2.06 (quin, 2H), 1.44 (s, 9H) $^{13}$C NMR (126 MHz, CDCl$_3$): δ155.97, 79.47, 38.96, 32.65, 30.89, 28.40.)

20 tri-tert-butyl 2,2',2"-(10-(3-((tert-butoxycarbonyl)amino)propyl)-1,4,7,10-tetraazacyclododecane-1,4,7-triyl)triacetate (8d)

DO3A-tris-tert-butyl ester.HBr was synthesized according to previously published procedures. DO3A-tris-tert-butyl ester.HBr (2.731 g, 4.6 mmol) and 8c (1.150 g, 4.8 mmol) were dissolved in 50 mL of MeCN. Anhydrous potassium carbonate (1.614 g, 11.7 mmol) was added and the reaction stirred overnight at 60° C. Reaction progress was monitored by mass spectrometry. The crude material was filtered, concentrated under reduced pressure, and purified by flash chromatography over silica gel using 1:9 MeOH:DCM (Pt stain) to give the product as an oily solid (2.526 g, 3.4 mmol, 82%). $^1$H NMR (500 MHz, CDCl$_3$): δ 3.64-2.29 (m, 22H), 1.65 (bs, 4H), 1.48-1.43 (m, 36H). $^{13}$C NMR (500 MHz, CDCl$_3$): δ 172.70, 155.96, 82.63, 82.28, 55.77, 51.77, 38.82, 37.86, 28.44, 28.01, 27.81, 26.84. ESI-MS (m/z): Calcd. for [M+H]$^+$: 671.5 Found: 671.8.

gadolinium(III)2,2',2"-(10-(3-(amino)propyl)-1,4,7,10-tetraazacyclododecane-1,4,7-tryl)triacetate (8)

An aqueous trifluoroacetic acid (TFA) solution, 30:1:1 (TFA:triethylsilane:H$_2$O) was added to 8d (0.241 g, 0.4 mmol) at room temperature. The resultant was stirred at room temperature overnight. Complete deprotection was observed after 18 hours. TFA was removed from the solution by purging with a stream of nitrogen and concentrating from water twice. Upon resuspension in 20 mL H$_2$O, Gd(III) acetate hydrate [Gd(CH$_3$CO)$_3$·xH$_2$O, 0.118 g, 0.4 mmol] was added and the pH of the solution adjusted with 1M NaOH and 1M HCl to 6.5. The resultant was stirred at 60° C. overnight. The crude mixture was purified by semi-preparative HPLC on a reverse phase C18 column, eluting using the following method: initial conditions of 0% B were held constant for 6 min, ramp to 12% B over 3 min, wash at 100% B for 5 min followed by return to 0% B. The product fractions (8.43-11.00 min by UV/vis at 200 nm and 210 nm) were collected and freeze-dried (0.122 g, 0.2 mmol 62%). Analytical LC-MS showed a single peak with m/z=558.6; ([M+H]$^+$).

Example 1i

Synthesis of 9

9 was synthesized following previously published procedures. (Manus, L. M.; Mastarone, D. J.; Waters, E. A.; Zhang, X.-Q.; Schultz-Sikma, E. A.; MacRenaris, K. W.; Ho, D.; Meade, T. J. Gd (III)-Nanodiamond Conjugates for MM Contrast Enhancement. *Nano Lett.* 2009, 10, 484-489.) ESI-MS (m/z) observed: 601.1990, calculated: 601.1979 [M+H]$^+$. Elemental Analysis calculated for Na[C20H36GdN5O6].H2O.TFA: C, 35.01; H, 5.21; N, 9.28. Found: C, 35.16; H, 5.39; N, 9.16.

Example 1j

Synthesis of 10

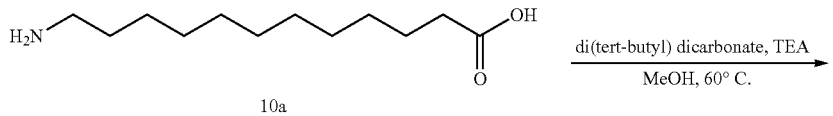

10a

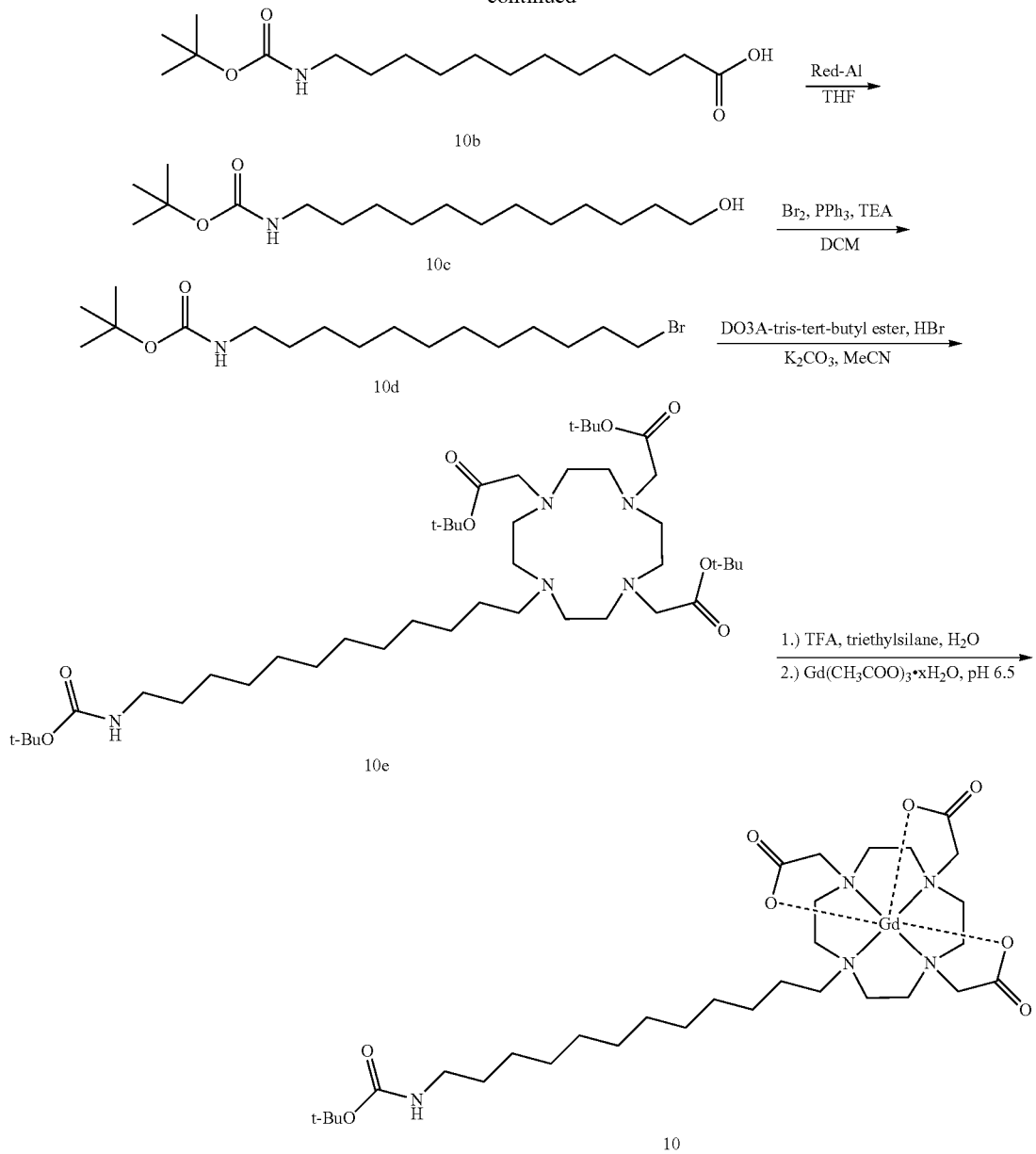

12-(N-tert-butoxycarbonyl)aminododecanoic acid (10b)

12-aminododeconic acid (10a, 1.066 g, 5.0 mmol), triethylamine (0.800 mL, 5.7 mmol), and boc anhydride (1.053 g, 4.8 mmol) were combined in 15 mL of MeOH and refluxed at 60° C. overnight. The reaction mixture was removed from heat and concentrated under reduced pressure. The resultant residue was redissolved in ethyl acetate, washed with 0.25 M HCl, dried over $MgSO_4$, filtered, and concentrated. The desired colorless, crystalline solid was obtained by recrystallizaton with hexanes (1.250 g, 4.0 mmol, 80%). $^1$H NMR (500 MHz, $CDCl_3$): δ0 4.54 (bs, 1H), 3.11 (2H, quar), 2.35 (t, 2H), 1.63 (quin, 2H), 1.45 (s, 11H), 1.27 (m, 14H). $^{13}$C NMR (126 MHz, $CDCl_3$): δ 179.08, 155.04, 79.11, 41.75, 40.64, 33.97, 30.03, 29.41, 29.33, 29.25, 29.17, 29.01, 28.44, 26.79, 24.70.

N-(tert-butoxycarbonyl)-12-hydroxydodecylamine (10c)

Boc-lauric acid (10b, 1.005 g, 3.2 mmol) was dissolved in 25 mL of tetrahydrofuran. Red-Al [70% (w/w) in toluene, 2.7 mL, 9.5 mmol] was added dropwise via syringe over 10 minutes at room temperature. The reaction mixture was stirred for thirty minutes after the precipitant dissolved (approximately 2 edit total). At this point, the reaction was quenched with a saturated solution of $Na_2SO_4$ (aq) followed by stirring for an additional 1 hour at room temperature. The resultant solution was concentrated under reduced pressure, resuspended in ethyl acetate, washed with water, dried over MgSO4, filtered, and concentrated. Recrystallizaton with toluene afforded a crystalline, colorless solid (0.663 g, 2.2 mmol, 86%). $^1$H NMR (500 MHz, $CDCl_3$): δ 4.54 (bs, 1H), 3.66 (t, 2H), 3.12 (quar, 2H), 1.68 (bs, 1H), 1.59 (quin, 2H), 1.46 (s, 11H), 1.29 (m, 16H). $^{13}$C NMR (126 MHz, CDCl$_3$): δ 156.01, 79.04, 63.09, 40.63, 32.81, 30.07, 29.58, 29.42, 29.29, 28.45, 26.81, 25.73.

N-(tert-butoxycarbonyl)-12-bromododecylamine (10d)

Triphenylphosphine (0.488 g, 1.9 mmol) was dissolved in 10 mL of dichloromethane and cooled to 0° C. Triethylamine (0.260 mL, 1.9 mmol) was added via syringe. Bromine (0.100 mL, 1.9 mmol) diluted in 15 mL of DCM was then added via syringe and the reaction vessel maintained at 0° C. for 1 hour. Upon warming to room temperature, 10c (0.5067 g, 1.7 mmol) in 6 mL of DCM was added and the reaction vessel stirred at room temperature overnight. Reaction progress was monitored by thin layer chromatography. The reaction volume was concentrated under reduced pressure followed by flash column chromatography purification of the crude material with ethyl acetate:hexanes (5:1) to give a colorless, crystalline solid (0.411 g, 1.1 mmol, 67%). Alternatively, the pure material can be obtained from recrystallizaton with acetonitrile. $^{1}$H NMR (500 MHz, CDCl$_3$): δ 4.61 (bs, 1H), 3.41 (t, 2H), 3.10 (quar, 2H), 1.85 (quin, 2H), 1.44 (m, 12H), 1.27 (m, 15H). $^{13}$C NMR (126 MHz, CDCl$_3$): δ 155.97, 78.91, 40.62, 34.04, 32.82, 30.05, 29.52, 29.50, 29.41, 29.28, 28.75, 28.42, 28.16, 26.80.

tri-tert-butyl 2,2',2"-(10-(12-(tert-butoxycarbonylamino)dodecyl)-1,4,7,10-tetraazacyclododecane-1,4,7-triyl)triacetate (10e)

Tris-tert-butyl DO3A.HBr (0.213 g, 0.4 mmol) and 10d (0.132 g, 0.4 mmol) were combined in acetonitrile (10 mL). Anhydrous potassium carbonate (0.126 g, 0.92 mmol) was added. The reaction was stirred at 60° C. for sixteen hours then cooled to room temperature and filtered rinsing with acetonitrile. The crude material was purified by flash column chromatography eluting with 1:9 methanol:dichoromethane (detected with Pt stain) and fractions concentrated to give a yellow oily solid (0.257 g, 0.3 mmol, 90%). $^{1}$H NMR (500 MHz, d$_6$-DMSO): δ 3.42-2.62 (m, 17H), 2.37-2.06 (m, 5H), 1.45-1.22 (m, 53H). $^{13}$C NMR (126 MHz, DMSO): δ 173.22, 172.59, 170.25, 166.93, 155.50, 131.57, 128.62, 81.64, 81.50, 80.55, 77.20, 67.32, 65.66, 55.85, 55.31, 53.89, 51.81, 49.82, 48.55, 38.02, 33.19, 26.21, 25.51, 23.91, 23.19, 22.38, 13.88, 10.78. ESI-MS (m/z): Calcd. for [M+H]$^-$: 797.6 Found: 798.7.

Gadolinium(III) 2,2',2"-(10-(12-(amino)dodecyl)-1,4,7,10-tetraazacyclododecane-1,4,7-tryl)triacetate (10)

An aqueous TFA solution, 30:1:1 (TFA:triethylsilane:H2O) was added to 10e (0.238 g, 0.3 mmol) at room temperature. The resultant was stirred at room temperature overnight. Deprotection was observed after 24 hours. TFA was removed from the solution by purging with a stream of nitrogen and concentrating from water twice. Upon resuspension in 20 mL H2O, Gd(CH$_2$COO)$_3$.xH$_2$O (0.104 g, 0.3 mol) was added and the pH of the solution adjusted with 1M NaOH and 1M HCl to 6.5. The resultant was stirred at room temperature until pH was maintained at 6.5. The crude mixture was purified by semipreperative HPLC on a reverse phase C8 Sunfire column, eluting using the following method: initial conditions of 5% B were held constant for 5 min, then a ramp to 100% B over 20 min, a wash at 100% B for 4 min followed by return to 5% B. The product fractions (11:45-16:45 mins by UV/vis at 200 nm and 220 nm) were collected and freeze-dried (0.055 g, 0.08 mmol, 27%). Analytical LC-MS showed a single peak with m/z=684.2 ([M+H]$^+$).

Example 1k

Magnevist [Gd(DTPA)(H$_2$O)] (11)

Diethylenetriaminepentaacetic acid gadolinium(III) dihydrogen salt hydrate was purchased from Sigma-Aldrich (Catalogue number 381667) and used as supplied. To make up a solution, Milli-Q water was added and the pH was adjusted to 7 using 2.0M NaOH.

Example 1l

Synthesis of 12

Magnevist-NH$_2$ (12) was synthesized following previously published procedures. (Hung, A. H.; Duch, M. C.; Parigi, G.; Rotz, M. W.; Manus, L. M.; Mastarone, D. J.; Dam, K. T.; Gits, C. C.; MacRenaris, K. W.; Luchinat, C.; et al. Mechanisms of Gadographene-Mediated Proton Spin Relaxation. *J. Phys. Chem. C* 2013, 117, 16263-16273.) ESI-MS (m/z) observed: 617.1, calculated: 617.1 [M]$^-$.

Example 1m

Synthesis of ProHance [Gd(HP-DO3A)(H$_2$O)] (13)

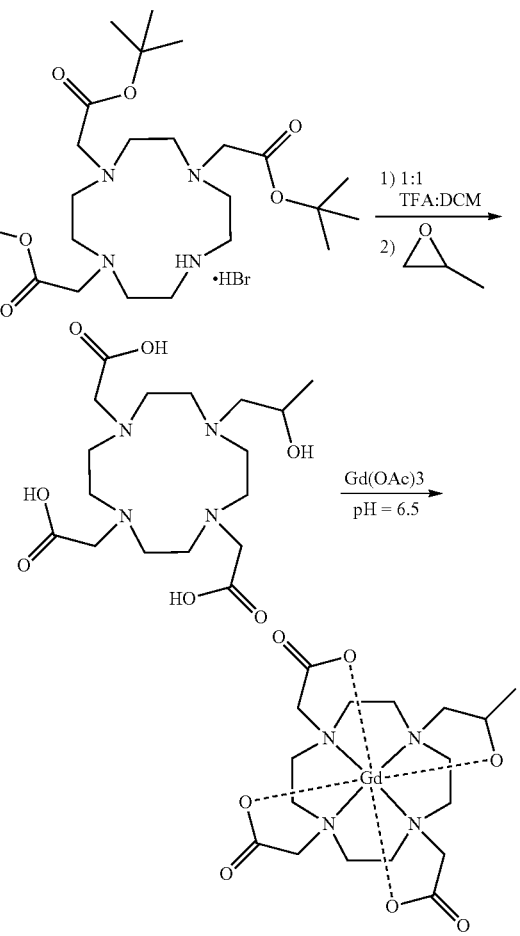

To a 100 mL round bottom flask charged with a magnetic stir bar and tert-butyl DO3A.HBr (0.278 g, 0.47 mmol) was added 1:1 trifluoroacetic acid and dichloromethane (25 mL). Upon addition of the solvent/acid mixture, the reaction turned a pale orange, transparent color and was left to stir for 12 hours at room temperature. After such time, all solvent was evaporated resulting in a pale brown oil. To verify complete deprotection, ESI-MS was used to observe the complete loss of starting material (product (m/z): observed: 346.1, calculated: 346.4 [M+H]$^+$). To the pale brown oil was added water (20 mL), and aqueous 1.25 M NaOH until the solution was pH=12. To this stirring, basic mixture was added propylene oxide (0.081 g, 1.40 mmol). The reaction was then left to stir for 12 hours at room temperature. The complete reaction of DO3A was verified by ESI-MS (product (m/z): observed: 405.7, calculated: 405.5 [M+H]$^-$). The mixture was then acidified using aqueous 1M HCl until the solution was pH=4. To the stirring, acidic mixture was added gadolinium(III) acetate hydrate (0.250 g, 0.75 mmol). The pH of the resulting solution was adjusted to pH=6.5 and monitored until stable using 1.25 M aqueous NaOH. The reaction was then left to stir for a further 12 hours at room temperature. The crude mixture was purified by semi-preparative reverse phase HPLC using the following conditions: 0-5 min 0% solvent B, 20 min 40% solvent B, 25 min 100% solvent B, 25-30 min 0% solvent B, 35 min 0% Solvent B and 35-40 min 0% solvent B. The desired product elutes from 15.9 to 16.6 minutes as monitored by UV-vis at 201/210 nm and was collected and lyophilized. Yield: 0.066 g (25%). (m/z): observed: 559.2, calculated: 559.7 [M–H]$^+$.

Example 1n

Synthesis of Dotarem [Gd(DOTA)(H$_2$O)](14)

Unmetalated DOTA ligand was purchased from Macrocyclics, Inc., and was metalated using the same procedure as prior to generate 13.

Example 2

Graphene Oxide Synthesis.

GO was synthesized using a modified Hummers method as previously reported. 115 mL of concentrated sulfuric acid (Mallinckrodt Baker) were cooled to 0° C. in an ice water bath. 5 g of natural graphite flakes (Asbury Graphite Mills, 3061 grade) were added to the cooled acid. 15 g of KMnO4 were then slowly added to the acid and graphite mixture with stirring and further cooling to keep the temperature below 20° C. The mixture was then heated and held at 35° C. for 2 hours under constant stirring. 230 mL of deionized water (DI) was then added to the mixture slowly to avoid a rapid increase in temperature. The reaction was terminated 15 minutes later by the further addition of 700 mL DI. Finally, 12.5 mL of 30% H2O2 was slowly added under constant stirring. The slurry was then vacuum filtered and washed with 1.25 L of 1:10 HCl solution to remove metal ions and other contaminants. Following washing, the solution was re-suspended in 500 mL DI and centrifuged for 12 h at 7500 rpm in an Avanti J-26XPI centrifuge (Beckman Coulter) with a JS-7.5 swinging bucket rotor to sediment the GO. The supernatant containing residual HCl was decanted. This wash step in DI water was repeated 6 times so that the final re-suspension in DI resulted in a pH 6 mixture. For the 150 nm GO, 90 mL batches of the re-suspended solution were ultrasonicated in 150 mL stainless steel beakers using a Fisher Scientific Model 500 Sonic Dismembrator with a ½" tip for 1 hr at 50% amplitude (~55 W) while cooled in an ice water bath. For the 1500 nm GO, 90 mL batches of the re-suspended solution were bath-sonicated for 1 hour. For both the 150 nm and the 1500 nm GO, a final centrifugation step of 5000 rpm for 10 minutes was performed to remove any unoxidized graphite.

Example 3

GO Characterization.

All GO samples were characterized using atomic force microscopy (AFM), Raman spectroscopy, and X-ray photoelectron spectroscopy (XPS). The mean and median of the sizes measured are summarized in Table 1. The relatively consistent height of 0.85 nm across both the 150 nm GO and the 1500 nm GO indicates that these samples are predominantly single layer sheets.

Raman spectroscopy and XPS were used to probe the chemical structures of GO. Comparing the Raman spectra of the 1500 nm GO to the 150 nm GO, the larger sample showed an increase in the D band relative to the G band, and a broadening of the 2D and G+D band areas (FIG. 2). This result is similar to that observed for GO after solvothermal reduction and that of graphene nanoribbons of increasing width. Furthermore, XPS showed that the ratio of carbon-carbon bonds (C—C) to carbon-oxygen bonds (C—O, C═O, C(O)O) increased with GO size. The fitted C—C:C—O:C═O:C(O)O distribution was 10:6.1:4.2:1.4 and 10:4.9:3.9:1.3 for the 150 nm and the 1500 nm GO, respectively (FIG. 3). The Raman and XPS data together indicate that the smaller GO bears fewer vacancy defects and 10%-15% more oxygen groups compared to the larger GO. That the smaller GO has comparatively more carbon-oxygen bonds than the larger GO may be explained by its larger edge-to-surface ratio. The edges of GO produced by the modified Hummers method are thought to be generously decorated with oxygen-containing functional groups. (Lerf, A.; He, H.; Forster, M.; Klinowski, J. Structure of Graphite Oxide Revisited. *The Journal of Physical Chemistry B* 1998, 102, 4477-4482; Gao, W.; Alemany, L. B.; Ci, L.; Ajayan, P. M. New Insights into the Structure and Reduction of Graphite Oxide. *Nat. Chem.* 2009, 1, 403-408.)

Example 4

Atomic Force Microscopy.

For sample preparation, GO was deposited onto silicon wafers with a 300 nm oxide layer as a substrate. The substrates were washed with acetone and isopropanol and thoroughly rinsed with DI water. They were then submerged in a 2.5 mM (3-aminopropyl) triethoxysilane (APTES) solution for 30 minutes. The substrates were then rinsed twice with DI water and dried with nitrogen. Immediately, 15 µL of 0.005-0.01 mg/mL GO solution was placed on the surface and left undisturbed for 10 minutes. The substrates were again rinsed twice with DI water and dried with nitrogen. The samples were annealed at 250° C. in air for 30 minutes to remove residual APTES. AFM was performed with a procedure reported elsewhere using a Thermo Microscopes Autoprobe CP-Research AFM in tapping mode with conical, symmetric tips (Budget Sensors, All-In-One, cantilever B).

Example 5

Raman Spectroscopy.

Sample preparation for Raman spectroscopy was performed as with the AFM samples except the final annealing step at 250° C. was omitted. Raman spectra were obtained using an Acton Tri Vista CRS Confocal Raman system with excitation radiation of an Ar-Kr 514.5 nm gas laser at a power of ~10 mW. Spectra were recorded in the range of 1100-3500 cm$^{-1}$ over several different GO sheets and samples. Backgrounds were subtracted and spectra were normalized for comparison.

Example 6

X-ray Photoelectron Spectroscopy.

For sample preparation, approximately 0.5 mg GO was vacuum filtered onto a 0.025 µm membrane (Millipore, CSWP) and rinsed with 10 mL DI. The filters were allowed to dry in air before measurement. XPS measurements were performed using a Thermo Scientific ESCALAB 250Xi system. Several spectra were recorded for each sample. Data was corrected for charge shifting and fitted using the Thermo Scientific Avantage Data System.

Example 7

Inductively Coupled Plasmon-Mass Spectrometry.

ICP-MS Samples were prepared in 15-mL conical tubes by adding ACS reagent grade nitric acid (70%), followed by incubation at 70° C. overnight to allow for complete sample digestion. The effectiveness of this digestion protocol was previously validated for GO. After incubation, a multi-element internal standard (containing Bi, Ho, In, Li, Sc, Tb, and Y, Inorganic Ventures, Christiansburg, Va.) and milli-Q water (18.2 MΩ·cm) were added to produce a final sample of 3% (v/v) nitric acid and 5 ng/mL internal standard.

ICP-MS was performed on a computer-controlled (Plasmalab software) Thermo X series II ICP-MS (Thermo Fisher Scientific, Waltham, Mass., USA) operating in standard mode equipped with an ESI SC-2 autosampler (Omaha, Nebr., USA). Each sample was acquired using 1 survey run (10 sweeps) and 3 main (peak jumping) runs (100 sweeps). The isotopes selected for analysis were Gd with In and Ho isotopes selected as internal standards for data interpolation. Instrument performance is optimized daily through an autotune followed by verification via a performance report (passing manufacturer specifications). Instrument calibration was accomplished by preparing individual-element Gd standards (Inorganic Ventures, Christiansburg, Va., USA) using concentrations of 0.78125, 1.5625, 3.125, 6.25, 12.50, 25.00, 50.00, 100.0, and 200.0 ng/mL containing 3.0% nitric acid (v/v) and 5.0 ng/mL of multi-element internal standard.

Example 8

Molecular Adsorption Assay.

Solutions of Gd(III)-labeled molecules were prepared by dissolving approximately 1 mg compound in 1 mL of Milli-Q water. The exact concentration of Gd in each sample was determined by ICP-MS. These solutions were then diluted to 1 mM Gd concentration and stored at 4° C. 150 nm and 1500 nm GO solutions were prepared by diluting the stock solutions to a concentration of 0.1 mg/mL as measured by UV-Vis absorbance at 300 nm (extinction coefficient 3650 mL mg$^{-1}$ m$^{-1}$).

To test adsorption, 75 µL of small molecule and 75 µL of GO were mixed together and left undisturbed for at least 15 minutes. 250 µL of MEM (Life Technologies, Carlsbad, Calif.) supplemented with 10% FBS (VWR Scientific, Radnor, Pa.) was then added to result in a 400 µL mixture. The ratios and volumes chosen replicate the conditions used in cell delivery experiments. The mixtures were gently rotated for 30-60 minutes, followed by centrifugation at 14,800 RPM for 20 minutes (Thermo Scientific, Model Legend Micro 21R). 385 µL, of supernatant was removed and saved for T2 relaxation time measurement. The pellet was re-suspended with 385 uL of 5:3 MEM:Milli-Q water. The centrifugation wash step was repeated until the $T_2$ relaxation time of the supernatant approximates that of 5:3 MEM:Milli-Q water without Gd (2300-2500 ms) as measured by a Bruker mq60 minispec relaxometer (Bruker Canada, Milton, Ontario, Canada). Typically, 3 washes were necessary to satisfy this criterion. After the final wash, all supernatant was removed and the pellet was re-suspended in 400 µL Milli-Q water to minimize UV-Vis interference. 200 µL of the final re-suspended solution was used to prepare ICP-MS samples for Gd concentration determination; the remaining 200 µL was measured by UV-Vis at 300 nm wavelength to determine GO concentration. For samples that flocculated, as evidenced by increased contribution from light scattering during UV-Vis measurement, the recorded absorbance was reduced by an empirical correction factor of 1.353.

A control experiment was performed for each of the 14 small molecules by replacing the 75 µL of GO with pure Milli-Q water. After the final wash, 385 µL of supernatant was removed and replaced with 385 µL Milli-Q water. 200 µL of the final solution was used to prepare ICP-MS samples for Gd concentration determination.

To calculate adsorption, Gd concentration of the control was subtracted from the Gd concentration of the Gd-GO mixtures. GO concentration was converted to carbon concentration by atomic mass. The carbon concentration was overestimated because oxygen was not taken into account in the conversion. Adsorption was obtained by taking the ratio of the corrected Gd concentration to the calculated carbon concentration.

Example 9

Alternative Molecular Adsorption Assay.

Figure 17:
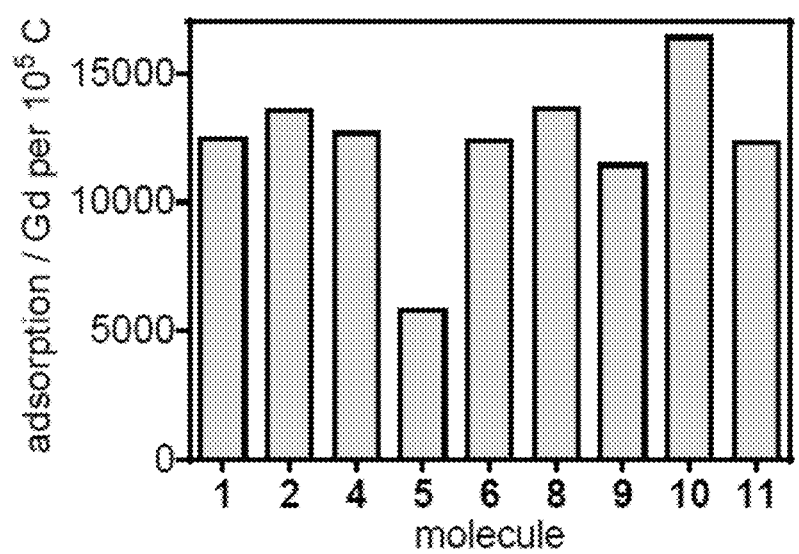
FIG. 17. Adsorption as characterized by measuring the amount of Gd left in the supernatant after the GO has been centrifuged into a pellet. These numbers are 30-1000 times greater than those measured directly from the pellet after washing. Direct measurement of adsorption on the GO pellet is considered to be the more reliable method of the two. The 150 nm GO was used for this experiment.

An alternative method of characterizing adsorption was investigated by measuring the amount of Gd remaining in supernatant after a single centrifugation at 14,800 RPM for 20 minutes. The difference in supernatant Gd concentration pre- and post-centrifugation was assumed to have been adsorbed to GO. Comparison showed a significant difference between the adsorption measured from the supernatant and the adsorption measured directly from the washed GO pellet (FIGS. 5A, 17). Direct measurement on the GO pellet was considered more accurate based on its predictive power for GO cell delivery enhancement.

Example 10

Adsorption Time Study.

For studies investigating zero adsorption time, 75 µL of GO was added to 250 µL of media, followed by the addition of 75 µL of the Gd(III)-labeled molecule. The solution was left undisturbed for at least 15 minutes before being transferred to a rotator. The rest of the study was performed following the procedures as already described.

Example 11

Octanol-Water Partition Coefficients.

Approximately 1 mg of each compound was dissolved in 1 mL of a 1:1 mixture of water/1-octanol. After shaking the sample tube vigorously for 30 s, the tube was placed on a rotator for gentle mixing over 6 h. The tube was then removed from the rotator and allowed to sit for 12 h to ensure complete separation of the aqueous and organic phases. Once separation was complete, 10 µL was removed from each layer to determine the phases. Once separation was complete, 10 µL was removed from each layer to determine the concentration of Gd by ICP-MS. The partition coefficient was calculated from the following equation: $\log_{10}P=\log_{10}(C_o/C_w)$, where $\log_{10} P$ is the logarithm of the partition coefficient, $C_o$ is the concentration of Gd in the 1-octanol layer, and $C_w$ is the concentration of Gd in the water layer.

Example 12

Sedimentation Assay.

Solutions of Gd(III)-labeled molecules were prepared by dissolving approximately 1 mg compound in 1 mL of Milli-Q water. The exact concentration of Gd in each sample was determined by ICP-MS. These solutions were then diluted to 1 mM Gd concentration and stored at 4° C. 150 nm and 1500 nm GO solutions were prepared by diluting the stock solutions to a concentration of 0.1 mg/mL as measured by UV-Vis absorbance at 300 nm (extinction coefficient 3650 mL $mg^{-1}$ $m^{-1}$).

In a 1.5-mL microcentrifuge tube, 75 µL of small molecule and 75 µL of GO were mixed together and left undisturbed for at least 15 minutes, followed by addition of 250 µL of MEM supplemented with 10% FBS to result in a 400 µL mixture. The ratios and volumes chosen replicate the conditions used in cell delivery experiments. After mixing, the solutions were gently rotated for 30-60 minutes. To measure sedimentation, the solutions were centrifuged for 10 minutes in a Model Legend Micro 21R centrifuge (Thermo Scientific) at predetermined speeds (e.g., 0, 2000, 4000, 6000, 8000 RPM). Following each round of centrifugation, 100 µL of supernatant was removed and measured with UV-Vis at 325 nm wavelength using 5:3 MEM/Milli-Q water as the blank. The supernatant was returned to the original solution and mixed using a pipette for another round of centrifugation at a different speed. A sedimentation curve was constructed by plotting the fraction of GO remaining in supernatant against centrifugation speed. Sedimentation was quantified by taking the area under the sedimentation curve (AUC), with more significant sedimentation being indicated by smaller AUC.

Example 13

General Cell Culture.

Dulbecco's modified phosphate buffered saline (DPBS), media, and dissociation reagents were purchased from Life Technologies (Carlsbad, Calif.). CorningBrand® cell culture consumables (flasks, plates, etc.) and sera were purchased from VWR Scientific (Radnor, Pa.). HeLa cells (ATCC® CCL-2™) and KB cells (ATCC® CCL-17™) were purchased from the American Type Culture Collection (ATCC, Manassas, Va.) and cultured in phenol red-free minimum essential media (MEM) supplemented with 10% fetal bovine serum (FBS). Prior to all experiments, cells were plated and allowed to incubate for 24 hours before dosing. Cells were harvested with 0.25% TrypLE for 5 minutes at 37° C. in a 5.0% $CO_2$ incubator. For sterilization, all Gd(III)-labeled molecules were filtered with 0.2 µm sterile filters prior to concentration determination and storage at 4° C. GO was used as prepared without further sterilization. Literature reports suggest that GO in water are inherently bactericidal. Cells were grown in a humidified incubator operating at 37° C. and 5.0% $CO_2$.

Example 14

Guava ViaCount Assay for Cell Counting.

Cell counting was conducted using a Guava EasyCyte Mini Personal Cell Analyzer (EMD Millipore, Billerica, Mass.). After cell harvesting, an aliquot (50 µL) of the cell suspensions was mixed with Guava ViaCount reagent (150 µL) and allowed to stain at room temperature for at least 5 minutes. The dilution factor of 4 was determined based upon optimum machine performance (20-150 cells/µL). After vortexing for 10 sec, stained cells were counted using a Guava EasyCyte Mini Personal Cell Analyzer (PCA) using the ViaCount software module. For each sample, 1000 events were acquired. Gating of live/dead and cell/debris classifications were performed manually by the operator. Instrument reproducibility was assessed biweekly using GuavaCheck Beads and following the manufacturer's suggested protocol using the Daily Check software module.

Example 15

Cellular Delivery Studies.

Cellular delivery studies were performed with HeLa and KB cells. HeLa and KB were plated at a cell density of approximately 25,000 and 50,000 cells per well, respectively, in a 24-well plate as counted by a hemocytometer. Stock solutions of 1-14 (1 mM), 150 nm GO (100 µg/mL), and 1500 nm GO (100 µg/mL) were prepared using sterile Milli-Q water. Prior to dosing, 80 µL (8.0 ng) of each GO (150 nm and 1500 nm) and 80 µL (80 nmol) of each Gd(III)-labeled molecule (1-14) were mixed and allowed to adsorb for at least 15 minutes. 150 µL Gd(III)-GO solutions were added to 250 µL media to give a final concentration of 188 µM Gd and 18.8 µg/mL GO. Cells were incubated with the mixture of Gd(III)-labeled molecules and GO for 24 edit. To harvest, cells were rinsed in-plate three times with 500 µL PBS plate three times with 500 µL PBS and trypsinized using 100 µL 0.25% TrypLE. Following trypsin treatment, 150 µL of media was added to each well and mixed by a pipette to ensure that all cells were lifted into suspension. 50 µL of the cell suspension was used for cell counting and 150 µL was used for Gd content analysis via ICP-MS.

For studies investigating zero adsorption time, 75 µL of GO was added to 250 µL of media, followed by the addition of 75 µL of the Gd(III)-labeled molecule. The mixture was left undisturbed for 15 minutes before being added to the cells. The rest of the study was performed following the procedures as already described.

To examine concentration-dependent delivery by GO, the concentration and ratio of Magnevist/150 nm GO were varied. Prior to dosing, stock solutions of 150 nm GO (107, 80, 53, 27, 13, and 0 µg/mL) and Magnevist (186.7, 93.3, 46.7, and 23.3 mM) were prepared. 80 µL of each concentration of GO and 80 µL of each concentration of Magnevist were mixed and allowed to adsorb for at least 15 minutes before adding to 250 µL media, creating a total of 24 separate conditions. The final concentrations of GO were 20, 15, 10, 5, 2.5, and 0 µg/mL; the final concentrations of Magnevist were 35, 17.5, 8.8, 4.4 mM. All other procedures were performed as already described.

Example 16

Robustness of GO Co-Incubation Protocol.

The robustness of the GO co-incubation protocol was evaluated in terms of 1) generalizability across cell lines, 2) inherent variability, and 3) sensitivity to procedural parameters.

Two molecular cargos, 9 and 11, were co-incubated with GO on KB and HeLa cells to assess the effect of cell line on GO delivery. The result showed similar delivery enhancement by GO regardless of the cell line used (FIG. 13), suggesting that GO co-incubation is indeed a delivery strategy that can be generalized beyond HeLa cells.

To characterize the inherent variability of the co-incubation protocol, the coefficient of variation (% CV) was used to measure data spread. % CV is defined as the ratio of the standard deviation to the mean. Beyond experimental error, inherent data spread arises due to complexities in cellular behavior, serum components, and nanomaterial synthesis. At 35 mM [Magnevist] and 20 µg/mL [GO], Magnevist uptake with and without GO resulted in 515±319 (62% CV over 17 trials) and 115±32 (28% CV over 10 trials) fmol Gd/cell, respectively (FIG. 14). The increased variability observed with GO co-incubation may be attributed to varying degrees of GO sedimentation across multiple experiments. The Magnevist-GO combination would be particularly susceptible to this type of variability because it exhibited only moderate sedimentation in media (FIG. 5B), making it possible for environmental factors such as cellular secretions or uncontrolled serum components to further induce sedimentation and change delivery. For variability in nanomaterial synthesis, a 23% CV in cell uptake was observed across three batches of GO (FIG. 14). Overall, the inherent variability found is smaller than the average delivery enhancement achieved with GO co-incubation. Therefore, while the degree of enhancement can vary from experiment to experiment, GO can consistently be expected to increase cellular delivery.

To characterize procedural robustness, variations were made to the standard cellular assay that used 25,000 cells per well in a 24-well plate with in-plate washing. From this baseline, it was found that increasing the cell density to 75,000 cells per well, assaying in a 6-well plate, and adding a centrifugation wash step lowered the cellular Gd(III) content by 53%, 39%, and 71%, respectively (FIG. 15). Similarly, using GO concentrations higher than 20 µg/mL resulted in a decrease in delivery, likely due to the formation of flocculants and aggregates that can interfere with cellular interaction and entry (FIG. 15). These procedural parameters evidently play a significant role in the GO co-incubation protocol and should not be overlooked in future experimental design.

As an example, cells used for MRI had lower Gd(III) contents compared to those from other studies due to a change in labeling vessel and the centrifugation step needed to control cell density. At 35 mM [Magnevist] and 20 µg/mL [GO], the typical cellular Gd(III) content was 299±67 fmol/cell with GO (N=11) and 91±9 fmol/cell without GO (N=4) (3.3× enhancement) (FIG. 14). In order to label a large number of cells for imaging, 6-well plates had to be used to replace the 24-well plates standard in the other studies. Moving from 24-well plates to 6-well plates decreased loading to 151±56 fmol/cell with GO (N=13) and 49±19 fmol/cell without GO (N=4) (3.1× enhancement). In order to control cell density for imaging, centrifugation was employed. The additional step resulted in the removal 60-70% of the Gd(III) labels, attributed to membrane binding (FIG. 15). In the imaging study, the loading achieved was 153 fmol/cell with GO and 69 fmol/cell without GO (2.2× enhancement) before centrifugation, and 47 fmol/cell with GO (69% label loss) and 30 fmol/cell without GO (57% label loss) after centrifugation.

Example 17

Statistical and Error Analysis.

Simple and multiple linear regression were performed using IBM SPSS Statistics software (ver. 19, IBM, New York, N.Y.). The $r^2$ reported are adjusted $r^2$ that take into account the number of explanatory variables in the model so that comparisons across different models are valid. Coefficients of variation (% CV) were calculated by taking the ratio of the standard deviation to the mean. For quantities that were calculated from several different raw measurements (e.g., adsorption and fold delivery enhancement), the errors were propagated according to the arithmetic operations performed. Where applicable, Table 5 lists the number of replicates and the % CV of each experiment.

TABLE 5

| Experimental Replicate Numbers | | |
|---|---|---|
| FIG. | N (range) | Average % CV |
| 5A adsorption (Gd/10⁵ C) | 3.5 (3-5) | 11% |
| 5B sedimentation (AUC) | 1.4 (1-2) | |
| 5C Gd content (fmol/cell) | 4.8 (3-11) | 25% |
| 9A Gd content (fmol/cell) | 5.2 (4-6) | 23% |
| 9C adsorption time | 3.7 (3-4) | 5 |

Example 18

Multiple Linear Regression Analysis.

Multiple linear regression was used to construct a predictive model of the fold delivery enhancement achievable for small molecules when GO is used as a co-incubation vehicle. The result of regression found molecular adsorption, GO sedimentation, and GO size to be significant explanatory factors of delivery. Higher adsorption, faster sedimentation, and smaller GO size enhanced delivery. To ensure that this conclusion did not result from a violation of the assumptions of multiple linear regression, the $r^2$ change of adding and removing factors, and the p value and the variance inflation factor (VIF) of each explanatory variable were examined.

The $r^2$ examined were adjusted $r^2$ that take into account the spurious increase in $r^2$ when extra explanatory factors are added to a model. When the explanatory factors adsorption, size, and sedimentation were added in order into the model, the $r^2$ increased from 0.67 to 0.71 to 0.92. In the final 3-factor model, all of the factors had a p value $<10^{-6}$ and a VIF <10. Multiple linear regression assumes a lack of collinearity among the explanatory factors, and a VIF below 10 confirms that the assumption has not been violated. Together, these results indicate that adsorption, sedimentation, and size all independently contribute to the predictive power of the final linear model.

For further validation, predictions made by the model can be confirmed qualitatively. First, adsorption was observed to increase delivery even for molecules that did not induce additional sedimentation (FIG. 8). This result held true for both sizes of GO, confirming that adsorption correlates with delivery enhancement independent of sedimentation and size. Second, although 8 exhibited reduced adsorption compared to 11 (FIG. 5A), it achieved a fold delivery enhancement that matched or even surpassed 11 upon GO co-incubation (FIG. 5C). This result can be attributed to the increased GO sedimentation that 8 induced compared to 11, confirming that sedimentation has power in explaining delivery enhancement independent of adsorption. Third, given the same level of sedimentation and adsorption (e.g., 10+150 nm GO and 10+1500 nm GO), the 150 nm GO outperformed the 1500 nm GO in delivery, confirming that size is an independent predictor of delivery enhancement. Thus, the 3-factor multiple linear regression model of GO delivery enhancement is validated both qualitatively and statistically.

Example 19

Cell MR Imaging.

HeLa cells were labeled by Magnevist with and without 150 nm GO co-incubation in 6-well plates. 2 plates seeded at 300,000 cells per well were needed to produce a sufficient number of cells for imaging. For the condition of GO co-incubation, 4500 μL of Magnevist-GO mixture was prepared at a concentration of 93.3 mM Magnevist and 27 μg/mL GO. The mixture was allowed to adsorb for at least 15 minutes. 375 μL of the Magnevist-GO mixture was added to 625 μL of media in each well to reach a final concentration of 35 mM Magnevist and 10 μg/mL GO. The cells were incubated with the mixture for 24 edit. To harvest, cells were rinsed in-plate three times with 3000 μL PBS and trypsinized using 400 μL 0.25% TrypLE. After 5 minutes of incubation at 37° C., 600 μL of media was added to each well and mixed by a pipette to ensure that all cells were lifted into suspension. After combining all the wells into a 12 mL cell suspension, 3 aliquots of 25 μL each were obtained for cell counting by Guava. 175 μL of Guava ViaCount reagent was used for dilution. Additionally, 200 μL of the cell suspension was transferred to a 1.5-mL microcentrifuge tube, centrifuged at 1000 RPM for 5 min (Thermo Scientific, Model Legend Micro 21R), and re-suspended in 200 μL media to wash the cells. From the washed cell suspension, two aliquots of 25 μL each were used for cell counting by Guava and two aliquots of 25 μL each were used for Gd content analysis by ICP-MS. For the condition without GO co-incubation, the same procedures were followed except GO was replaced by Milli-Q water.

To create the cellular phantoms in agarose, a 1% media-agarose was prepared by mixing media and 2% low melting-point agarose (Life Technologies, Carlsbad, Calif.) in equal parts. At 7 T, the media-agrose has a $T_1$ of 2952±152 ms and a $T_2$ of 96±1 ms. In a 4 mL 15×45 mm glass vial, 2 mL of media-agarose was gelled at room temperature around a 5 mm OD NMR tube that was later removed to create a cylindrical bore. To fill the bore, the suspension of labeled cells was centrifuged at 1000 RPM for 5 minutes. After removing the supernatant, the cell pellet was re-suspended in media-agarose and further diluted to densities of 10,000, 5,000, 2,000, 500, and 100 cells/μL. 300 μL of each cell suspension was used to fill the bores in the 4 mL vials. After filling, the vials were cooled to 4° C. for 20 minutes to solidify the suspension. Approximately 3 mL of media was added on top of the media-agarose to completely fill the vial.

$T_1$- and $T_2$-weighted imaging were performed on a Bruker Pharmscan 7.05 T imaging spectrometer fitted with shielded gradient coils and a RF RES 300 1H 089/023 quadrature transceiver volume coil at 25° C. (Bruker BioSpin, Billerica, Mass.). Imaging was performed using a Rapid Acquisition with Refocused Echoes (RARE) pulse sequence. For $T_1$-weighted imaging, the imaging parameters were TR=200 ms, TE=11.7 ms, NEX=1, FOV=21×21 mm$^2$, slice thickness=2 mm, and matrix size=256×256. For $T_2$-weighted HDR, the imaging parameters were TR=5000 ms, $T_E$=100 ms, NEX=1, FOV=15×15 mm$^2$, slice thickness=2 mm, and matrix size=256×256. The signal intensities of the acquired images were normalized such that the blank media-agarose has the same intensity across all images. Image processing was performed using ImageJ (NIH, Bethesda, Md.). $T_1$ and $T_2$-weighted images were processed separately.

As demonstrated, GO co-incubation enhances the cellular delivery of a variety of hydrophilic small molecules in culture. The strategy is simple, inexpensive, and requires no synthetic expertise. High degrees of enhancement up to 13 fold were achieved for molecules that adsorbed strongly and induced sedimentation. Adsorption was found to most prominently increase with amines over alkyls, hydroxyls, phosphates, carboxyls, quaternary ammoniums, and benzyls. GO with a lateral dimension of 150 nm achieved intrinsically higher cellular delivery compared to its 1500 nm counterpart independent of sedimentation. Compared to using purified nanocomplexes, co-incubation allowed for a 100-fold increase in cargo incubation concentration. As a direct consequence, GO co-incubation circumvented a key shortcoming of other nanomaterial solutions in the application of Gd(III) cellular NMI.

We claim:

1. A method of bioactive molecule delivery, comprising:
    incubating cells with a co-incubation medium for 24 hours to deliver a bioactive molecular component into the cells, wherein said co-incubation medium comprises functionalized graphene oxide (GO) having said bioactive molecular component adsorbed on a surface of graphene oxide, wherein said bioactive molecular component consists of Gd(III)-labeled molecules; and
    enhancing delivery of said bioactive molecular component into the cells by GO sedimentation.

2. The method of claim 1, wherein said Gd(III)-labeled molecules comprise a moiety selected from alkyl, amine, hydroxy, phosphate, carboxy, quaternary amine and aminoalkyl moieties, and combinations thereof.

3. The method of claim 1, wherein said graphene oxide has a lateral surface dimension of less than 1500 nm.

4. The method of claim 3, wherein said lateral surface dimension is 150 nm.

5. A method of bioactive molecule delivery, comprising:
    incubating cells with a co-incubation medium for a period of time to deliver a bioactive molecular component into the cells, wherein said co-incubation medium comprises functionalized graphene oxide (GO) having said bioactive molecular component adsorbed on a surface of graphene oxide, wherein said bioactive molecular component consists of Gd(III)-labeled molecules, and wherein the concentrations of Gd(III) and GO in said co-incubation medium are 188 μM and 18.8 μg/mL, respectively.

6. The method of claim 1, wherein said cells comprise HeLa cells and/or KB cells.

7. The method of claim 1, wherein said co-incubation medium has a Gd(III)-labeled molecule-to-GO ratio of 2.1× 10$^6$ Gd/10$^5$ C.

8. The method of claim 5, wherein the period of time is 24 hours.

* * * * *